US008204565B2

(12) United States Patent
Arnold et al.

(10) Patent No.: US 8,204,565 B2
(45) Date of Patent: Jun. 19, 2012

(54) REAGENTLESS OPTICAL ANALYTE DETECTION SYSTEM

(75) Inventors: Mark A. Arnold, Iowa City, IA (US); Jonathon T. Olesberg, Iowa City, IA (US); Chris Coretsopoulos, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1625 days.

(21) Appl. No.: 11/397,927

(22) Filed: Apr. 4, 2006

(65) Prior Publication Data

US 2007/0066877 A1 Mar. 22, 2007

Related U.S. Application Data

(60) Provisional application No. 60/667,973, filed on Apr. 4, 2005.

(51) Int. Cl.
*A61B 5/1455* (2006.01)
(52) U.S. Cl. .................................. 600/310; 600/316
(58) Field of Classification Search ........... 600/309–344
See application file for complete search history.

(56) References Cited

U.S. PATENT DOCUMENTS

| | | | | |
|---|---|---|---|---|
| 3,906,241 A * | 9/1975 | Thompson | ........... | 250/574 |
| 4,890,621 A * | 1/1990 | Hakky | ........... | 600/316 |
| 5,176,632 A | 1/1993 | Bernardi | ........... | 604/66 |
| 5,833,603 A | 11/1998 | Kovacs et al. | ........... | 600/317 |
| 5,842,981 A | 12/1998 | Larsen et al. | ........... | 600/323 |
| 6,049,727 A * | 4/2000 | Crothall | ........... | 600/310 |
| 6,546,268 B1 | 4/2003 | Ishikawa et al. | ........... | 600/345 |
| 7,116,419 B1 * | 10/2006 | Weiner et al. | ........... | 356/364 |
| 2001/0041831 A1 | 11/2001 | Starkweather et al. | ........... | 600/365 |
| 2002/0026108 A1 | 2/2002 | Colvin, Jr. | ........... | 600/316 |
| 2004/0051113 A1 * | 3/2004 | Chang et al. | ........... | 257/104 |
| 2005/0010087 A1 | 1/2005 | Banet et al. | ........... | 600/300 |
| 2005/0033127 A1 * | 2/2005 | Ciurczak et al. | ........... | 600/316 |
| 2005/0038326 A1 | 2/2005 | Mathur | ........... | 600/300 |
| 2005/0046850 A1 * | 3/2005 | Chow | ........... | 356/430 |
| 2005/0269499 A1 * | 12/2005 | Jones et al. | ........... | 250/269.1 |
| 2006/0264897 A1 * | 11/2006 | Lobl et al. | ........... | 604/506 |

OTHER PUBLICATIONS

Restriction Requirement dated Sep. 26, 2008, issued in U.S. Appl. No. 11/348,615.
Response to Restriction Requirement dated Feb. 26, 2009, filed in U.S. Appl. No. 11/348,615.

(Continued)

*Primary Examiner* — Eric Winakur
*Assistant Examiner* — Marjan Fardanesh
(74) *Attorney, Agent, or Firm* — Ballard Spahr LLP

(57) ABSTRACT

Disclosed is an implantable microspectrometer for the reagentless optical detection of an analyte in a sample fluid. The microspectrometer comprises an optical sampling cell having a cell housing defining a fluid inlet port and a fluid outlet port, the fluid inlet port configured to receive an optical sampling fluid from a test subject; an electromagnetic radiation source in communication with a first portion of the optical sampling cell housing and configured to irradiate at least a portion of the optical sampling fluid with electromagnetic radiation; and an electromagnetic radiation detector in communication with a second portion of the optical sampling cell housing and configured to detect electromagnetic radiation emanating from the optical sampling cell. In use, the implantable microspectrometer can optically detect at least one parameter of an analyte contained within the optical sampling fluid in the absence of an added reagent.

48 Claims, 20 Drawing Sheets

OTHER PUBLICATIONS

Non-Final Office Action dated Mar. 17, 2009, issued in U.S. Appl. No. 11/348,615.

Response to Non-Final Office Action dated Jun. 17, 2009, filed in U.S. Appl. No. 11/348,615.

Final Office Action dated Sep. 10, 2009, issued in U.S. Appl. No. 11/348,615.

Chaurasia C.S., In vivo microdialysis sampling: theory and applications. *Biomedical Chromatography* 13(5):317-32, 1999.

NIH Grant Application for Grant DK-64569 (Abstract and Application pp. 49-79).

Ihde, et al. Poster presentation for University of Iowa, Optical Science and Technology Center (Apr. 2, 2004).

Kanukurthy, et al. "Controller for a Continuous Near Infrared Glucose Sensor", Sensors for Industry Conference in Houston, Texas, USA (Feb. 2005).

Olesberg, Jonathon T. Electrochemical Society Powerpoint Presentation, "Application of Long-Wavelength Sources and Detectors for Medical Monitoring". The University of Iowa, Optical Science and Technology Center and the Department of Chemistry (May 12, 2004).

Rooyackers O, Thorell A, Nygren J, Ljungqvist O. Microdialysis methods for measuring human metabolism. *Current Opinion in Clinical Nutrition & Metabolic Care.* 7(5):515-21, 2004.

\* cited by examiner

REAGENTLESS OPTICAL ANALYTE DETECTION SYSTEM

CROSS REFERENCE TO RELATED APPLICATIONS

This application claims priority to and the benefit of U.S. Provisional Patent Application Ser. No. 60/667,973 filed in the United States Patent and Trademark Office on Apr. 4, 2005, the disclosure of which is hereby incorporated by reference in its entirety for all purposes.

STATEMENT OF GOVERNMENT SUPPORT

The invention described in the foregoing specification has been developed in part with funds received from the National Institutes of Health under grant number DK-64569. The United States Government may have certain rights under this invention.

FIELD OF THE INVENTION

The present invention relates generally to the field of analyte detection systems and more particularly to a reagentless optical analyte detection system.

BACKGROUND OF THE INVENTION

Diabetes is a chronic, incurable disease that causes an array of serious medical complications and even premature death. Complications include heart disease, stroke, kidney failure, and nervous system disorders. Although diabetes is a potentially devastating disease, early diagnosis and tight glycemic control can greatly diminish the medical complications and cost of this disease.

The goal of tight control is to maintain one's blood glucose levels within a physiologically acceptable range. Tight control therefore typically requires frequent blood glucose measurements, which provides the information needed to administer insulin or glucose properly. The pain, cost and inconvenience of state-of-the-art glucose monitoring technology impede frequent monitoring and are primarily responsible for the failure of patients to maintain tight control. Thus, it has been recognized for several decades that an ideal treatment of diabetes would involve a closed-loop insulin delivery system that is implanted within the patient's body.

This so-called artificial pancreas could comprise an insulin delivery pump coupled with some type of glucose-sensing technology. Using this system, insulin could be delivered continuously in response to detected changes in the blood glucose concentrations. However, for this system to be operable, the glucose sensing component must be able to provide accurate and rapid blood glucose values to a micro-processing unit, which would compute the amount of insulin required and then control the required insulin delivery. Accordingly, the successful development of an artificial pancreas or other artificial biological delivery system as described above depends on the development of implantable analyte (i.e., glucose) sensing technology and corresponding electronic support that can reliably control the instrumentation. Thus, there is a need in the art for implantable analyte sensing technology and electronic support that can enable the continuous operation of an analyte detection system for extended durations with minimal or even no user intervention required.

SUMMARY OF THE INVENTION

The present invention is based, in part, upon the invention of a reagentless optical analyte detection system. In one aspect, the reagentless optical analyte detection system can enable continuous and reagentless operation for extended periods of time with minimal or even no user intervention required.

In one aspect, the present invention provides an implantable microspectrometer, comprising an optical sampling cell having a cell housing defining a fluid inlet port and a fluid outlet port, wherein the fluid inlet port can be configured to receive an optical sampling fluid from a test subject. An electromagnetic radiation source is positioned in communication with a first portion of the optical sampling cell housing and configured to irradiate at least a portion of the optical sampling fluid with electromagnetic radiation. An electromagnetic radiation detector is also positioned in communication with a second portion of the optical sampling cell housing and configured to detect electromagnetic radiation emanating from the optical sampling cell.

In another aspect, the present invention provides an implantable microspectrometer, comprising an optical sampling cell having a cell housing defining a fluid inlet port and a fluid outlet port, wherein the fluid inlet port can be configured to receive an optical sampling fluid from a test subject. A means for generating electromagnetic radiation is provided whereby the means for generating radiation is in communication with a first portion of the optical sampling cell housing and configured to irradiate at least a portion of the optical sampling fluid with electromagnetic radiation. A means for detecting electromagnetic radiation is also provided, whereby the means for detecting electromagnetic radiation is in communication with a second portion of the optical sampling cell housing and configured to detect electromagnetic radiation emanating from the optical sampling cell.

According to various aspect, a microspectrometer of the present invention and as summarized herein is capable of irradiating a fluid sample with electromagnetic radiation and subsequently detecting variations in the electromagnetic radiation resulting at least from the interaction of the electromagnetic radiation with the fluid sample and, in particular, with a target analyte contained in the fluid sample. In another aspect, the analyte detection system can enable the continuous and reagent-free optical analysis of a sample fluid obtained from a test subject for extended periods of time without the need for user intervention.

In still another aspect, the present invention provides a method for the reagentless optical detection of an analyte in a fluid sample, comprising the steps of: providing a microspectrometer, comprising: (i) an optical sampling cell having a cell housing defining a fluid inlet port and a fluid outlet port, the fluid inlet port; (ii) an electromagnetic radiation source in communication with a first portion of the optical sampling cell housing; and (iii) an electromagnetic radiation detector in communication with a second portion of the optical sampling cell housing; obtaining a fluid sample containing an analyte from a test subject; conveying the obtained fluid sample through the inlet port in to the optical sampling cell; generating electromagnetic radiation from the electromagnetic radiation source and irradiating at least a portion of the fluid sample within the optical sampling cell; optically detecting electromagnetic radiation emanating from the optical sampling cell with the electromagnetic radiation detector; and optionally returning at least a portion of the obtained fluid sample contained within the optical sampling cell to the test subject.

Additional aspects of the invention will be set forth, in part, in the detailed description, figures and any claims which follow, and in part will be derived from the detailed description, or may be learned by practice of the invention. It is to be understood that both the foregoing general description and the following detailed description are exemplary and explanatory only and are not restrictive of the invention as disclosed.

BRIEF DESCRIPTION OF THE FIGURES

The accompanying drawings, which are incorporated in and constitute a part of this specification, illustrate several embodiments of the instant invention and together with the description, serve to explain, without limitation, the principles of the invention.

DETAILED DESCRIPTION OF THE INVENTION

Figure 1:
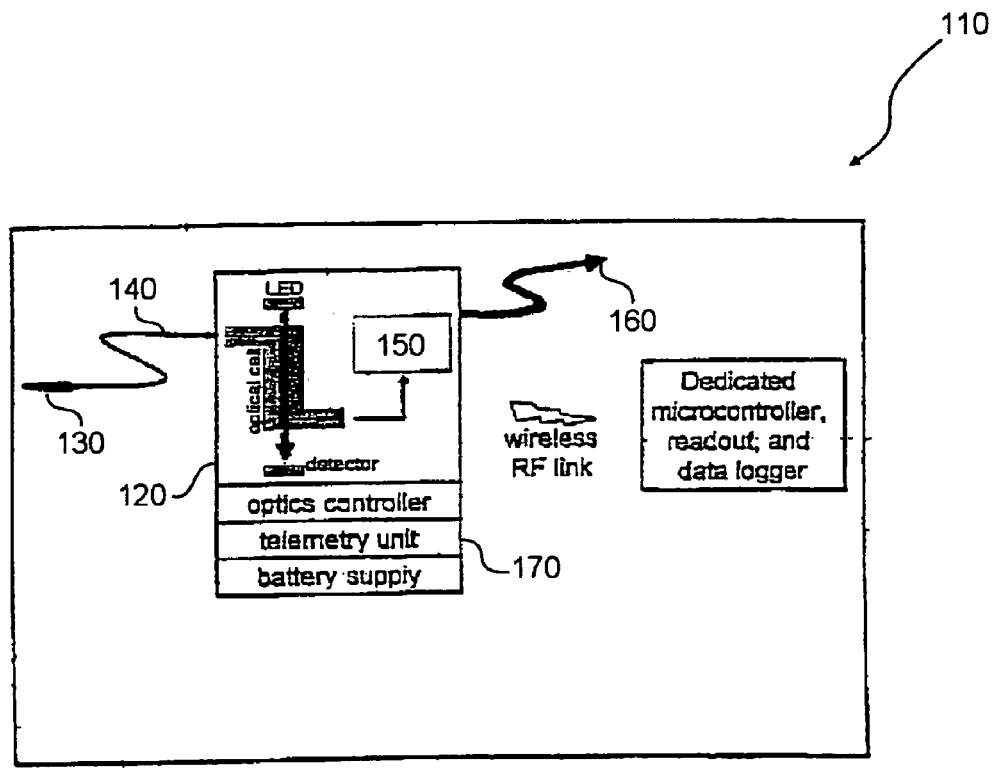
FIG. 1 illustrates a schematic view of a reagentless optical analyte detection system according to one aspect of the instant invention.

The present invention may be understood more readily by reference to the following detailed description, and figures, and their previous and following description.

Before the present compositions, devices, and/or methods are disclosed and described, it is to be understood that this invention is not limited to the specific articles, devices, and/or methods disclosed unless otherwise specified, as such may, of course, vary. It is also to be understood that the terminology used herein is for the purpose of describing particular aspects only and is not intended to be limiting.

As used herein, the singular forms "a," "an" and "the" include plural referents unless the context clearly dictates otherwise. Thus, for example, reference to an "analyte" includes aspects having two or more such analytes unless the context clearly indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, the term "tissue" includes an aggregate of cells of a particular kind, together with their intercellular substance, that forms a structural material.

As used herein, the term "interstitial" means relating to or situated in the small, narrow spaces between tissues or parts of an organ. Interstitial fluid is an extracellular fluid that is prevalent throughout the body and the skin. Because interstitial fluid is found in the outermost layers of the skin where there are fewer nerve endings, relatively painless samples can be obtained.

As used herein, "analyte" includes any physiological chemical having a functional group and/or chemical bond capable of providing an identifiable spectral signature or feature when irradiated with electromagnetic radiation, such as radiation in the near infrared (NIR) and/or middle infrared (MIR) wavebands. In one aspect, the functional group and/or chemical bond can be C—H, N—H, O—H, or any combination thereof. Specific and non-limiting examples of suitable analytes according to the instant invention include glucose, urea, lactate, creatinine, triglyceride, protein, cholesterol, and ethanol. In one aspect, the analyte is glucose. In still another aspect, the analyte is urea. In another aspect, an analyte is any target molecule capable of freely passing from blood into the interstitial fluid of a test subject. To this end, it should be appreciated that the present invention is not limited to use in connection with any one particular analyte or group of analytes.

As used herein, the term physiological "lag time" in one aspect refers to the delay or time differential in the equilibration between the concentration of a target analyte in interstitial fluid and the concentration of the same target analyte in blood. One of skill in the art will appreciate that the "lag time" of, for example, glucose in interstitial fluid, will vary depending on physiologic conditions. In another aspect, a so called instrumental "lag time" refers to the delay or time differential between the actual concentration of a target analyte in the interstitial fluid of a test subject and the concentration of the same analyte in a sample of interstitial fluid that is analyzed in the optical cell of a microspectrometer described herein. One of skill in the art will appreciate that instrumental lag time can be dependent, in part, on fluid dynamics and the flow rate of a sample stream within a microspectrometer as described herein. In still another aspect, it will be appreciated that a net "lag time" can refer to the combination of physiological and instrumental lag times as described herein. To this end, in one aspect, a net lag time can be used to calibrate, for example, an artificial pancreas.

As used herein, the term "test subject" includes any living organism from which a sample of interstitial fluid or any other sample fluid containing a target analyte can be obtained. In one aspect, a test subject can be any living organism in which an analyte detection system or any component thereof can be implanted in the subcutaneous tissue thereof. For example, in one aspect a test subject can be a plant. Alternatively, in another aspect, the test subject can be an animal. In one aspect the animal can be mammalian. In an alternative aspect the animal can be non-mammalian. The animal can also be a cold-blooded animal, such as a fish, a reptile, or an amphibian. Alternatively, the animal can be a warm-blooded animal, such as a human, a farm animal, a domestic animal, or even a laboratory animal. Accordingly, it should be understood that the present invention is not limited to its use in connection with any one particular test subject or group of test subjects.

As briefly stated above, the present invention is based, in part, upon the invention of a reagentless optical analyte detection system. To this end, in one aspect, the detection system can enable the continuous and reagent-free optical analysis of a sample fluid, such as interstitial fluid (ISF), sampled from a test subject for extended periods of time without requiring user intervention. Thus, it will be appreciated upon practicing the present invention that the reagentless analyte detection system can provide continuous analyte detection and analysis without resulting in the formation of reaction byproducts that have until now prevented the return of the analytical sample to the body or tissue of the test subject and which have needed to be stored, recycled or otherwise disposed of.

Referring specifically to FIG. 1, a schematic diagram of an exemplary and non-limiting analyte detection system 110 according to one aspect of the present invention is shown. The exemplified system is comprised of an integrated solid-state microspectrometer 120 that is capable of irradiating a sample of interstitial fluid delivered to an optical cell with electromagnetic radiation. The microspectrometer 120 can subsequently detect variations in the electromagnetic radiation resulting at least from the interaction of the electromagnetic radiation with the interstitial fluid. Interstitial fluid can be obtained by a sampling assembly 130 and subsequently conveyed to the optical cell of the microspectrometer 120 through a microfluidic channel 140. In one aspect, the interstitial fluid is drawn into the sampling assembly and propagated through the microfluidic pathway using a negative pressure gradient produced by a vacuum source 150. Once the sample has been analyzed by the microspectrometer 120, the sample can then be returned to the test subject or disposed of externally through an exit port 160. As further illustrated, the detection system can be coupled to one or more components of an electronic support unit (ESU) 170, which can provide electronic support for the detection system. In one aspect, the ESU can provide a power supply for the optical components of the microspectrometer and/or the vacuum source. In another aspect, the ESU can provide a means for transmitting spectroscopic data generated by the microspectrometer downstream for further processing.

Figure 2:
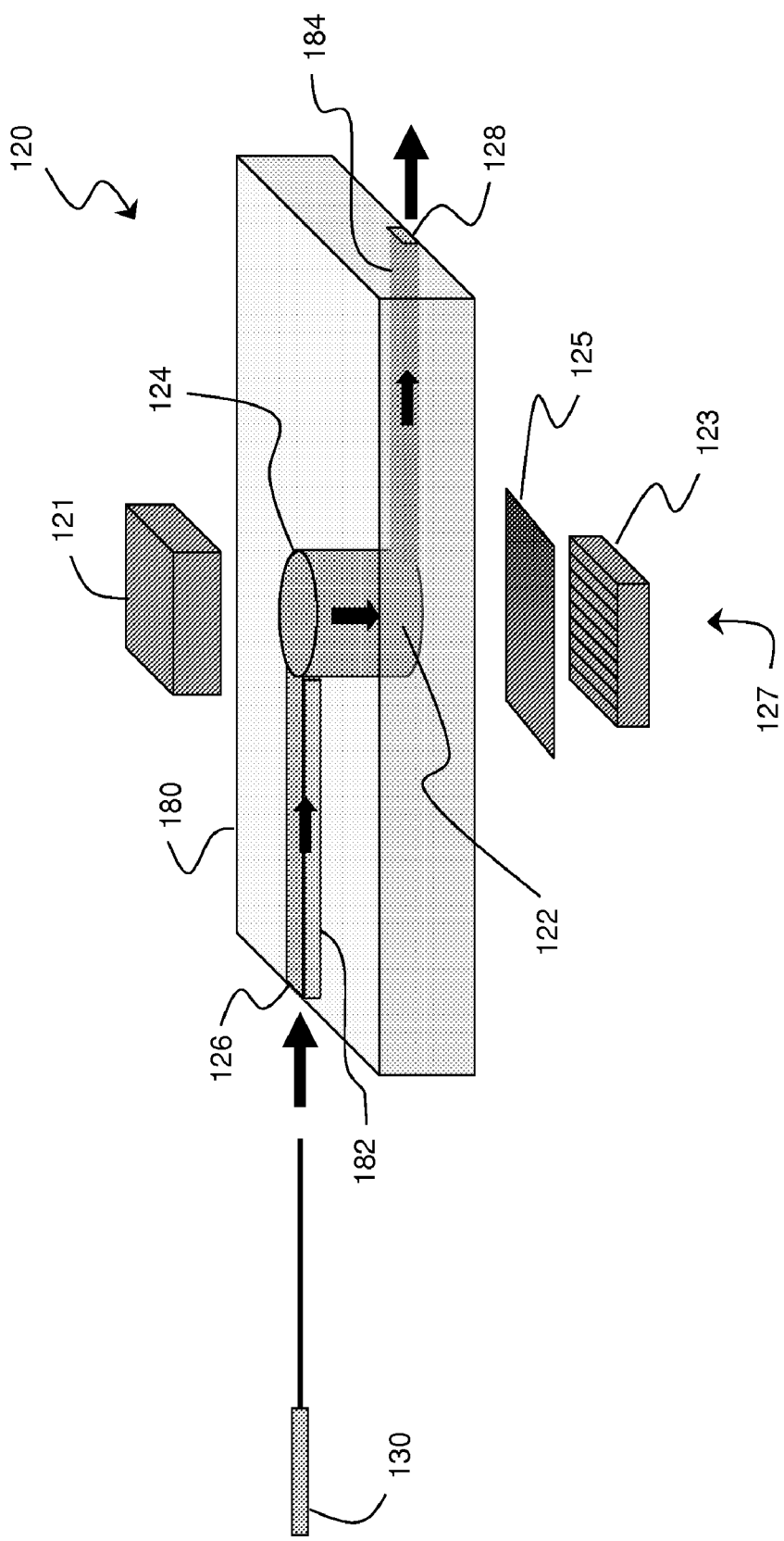
FIG. 2 illustrates a perspective view of microspectrometer according to one aspect of the present invention.

In one aspect, and as exemplified in FIG. 2, the analyte detection system of the present invention can comprise an implantable microspectrometer 120, comprising an optical sampling cell 122 having a cell housing 124 defining a fluid inlet port 126 and a fluid outlet port 128, wherein the fluid inlet port can be configured to receive an optical sampling fluid from a test subject. An electromagnetic radiation source 121 can be positioned in communication with at least a first portion of the optical sampling cell housing and configured to irradiate at least a portion of an optical sampling fluid with electromagnetic radiation. Still further, an electromagnetic radiation detector assembly 127 can be positioned in communication with at least a second portion of the optical sampling cell housing and configured to detect electromagnetic radiation emanating from the optical sampling cell. In one aspect, the implantable microspectrometer 120 can be configured to optically detect at least one parameter of an analyte contained within the optical sampling fluid in the absence of a reagent. In use, a sample of interstitial fluid can be delivered to the optical cell. The microspectrometer according to this aspect is capable of irradiating the sample of interstitial fluid with electromagnetic radiation generated by, for example, an electromagnetic radiation source and subsequently detecting electromagnetic radiation emanating from the optical sampling cell.

The microspectrometer of the instant invention can, in one aspect, be configured to measure the absorption spectra resulting from the interaction of the electromagnetic radiation with a sample. In an alternative aspect, the microspectrometer of the instant invention can be configured to measure the scattering spectra using conventional Raman spectroscopy techniques. As such, there are several conventional methods that can be used for performing spectrally resolved measurements on electromagnetic radiation that passes through the optical sampling chamber of a spectrometer including, without limitation, Fourier transform and dispersive techniques (utilizing diffraction gratings or dispersive prisms).

While any of these methods can be used in connection with the present invention, in one aspect, the microspectrometer according to the present invention is configured to measure infrared absorption spectra. According to this exemplary aspect, and as further depicted in FIG. 2, an exemplary microspectrometer can provide a spectrally resolved measurement using a spectroscopy system comprised of a high efficiency solid state broadband light source and a solid state photodetector assembly 127 comprised of a spatially variable bandpass filter 125 mounted on a photodiode array 123. As one of skill in the art will appreciate, the use of a photodiode array can allow for the real-time collection of a signal simultaneously at all wavelengths within the band of interest. The photodetector array can further convert the detected light signal to electrical signals or photo currents, which can then be passed downstream and analyzed by a processing system.

According to this exemplary spectroscopy system, light exiting the optical sampling chamber will be incident on the bandpass filter. The filter can be configured such that the central wavelength of the passband varies along one of the dimensions of the filter. Thus, each photodetector element, or photodiode, can be adapted to be sensitive to a different wavelength of light. Spectral resolution can then be determined from a combination of the width of the filter passband at each point and the width and packing separation distance of detector elements. The spectral point spacing can be determined from the number of detector array elements. It will be appreciated that a detector assembly can comprise any number of individual photodetector elements, depending on the spectral resolution necessary for obtaining sound analytical measurements. For example, an array of 16, 24, 32, or even 64 photodetector elements can be used. In one aspect, the electromagnetic radiation detector assembly 127 can comprise an array 123 of 32 photodiodes, as exemplified in FIG. 3.

Unlike conventional diffraction-based instruments, this exemplary and non-limiting spectroscopy system does not require the use of imaging optics. Thus, the bandpass filter and detector assembly can be mounted directly on the output region of an optical sampling cell, eliminating the need for free space coupling and enhancing the brightness and efficiency of the light source. Accordingly, in one aspect, the present invention provides a rugged, compact and durable spectrometer that can, for example, better suited for implantation into a test subject than conventional spectroscopy techniques.

It should also be understood that a microspectrometer according to the present invention is not limited to use in connection with a particular waveband in the infrared spectrum. Thus, in one aspect, the microspectrometer can be configured to operate in the near infrared electromagnetic region, including radiation in the wave number range of from approximately 4000 $cm^{-1}$ to approximately 14500 $cm^{-1}$. To this end, the microspectrometer can be configured to operate in additional wave numbers of 4000, 4500, 5000, 5500, 6000, 6500, 7000, 7500, 8000, 8500, 9000, 9500, 10000, 10500, 11000, 11500, 12000, 12500, 13000, 13500 and 14000 $cm^{-1}$ and any range derived from these values.

For example, and without limitation, when used in connection with an aqueous environment or aqueous sample such as the interstitial fluid obtained from the human body, the microspectrometer can be configured to operate in the so-called combination spectral range of the near infrared spectrum over a wavenumber range from approximately 4000 $cm^{-1}$ to approximately 5000 $cm^{-1}$. As one of ordinary skill in the art will appreciate, spectral features in the combination spectral range originate from the combination of stretching and bending vibrational modes associated with C—H, O—H, and N—H chemical bonds within the molecules in a sample matrix. In still another aspect, and again for exemplary aqueous samples, the microspectrometer can operate in the so-called first overtone spectral region of the near infrared spectrum over the wavenumber range from approximately 5500 $cm^{-1}$ to approximately 6500 $cm^{-1}$. Spectral features in this first overtone spectral range can correspond to the first overtone of C—H chemical bonds within these sample molecules.

In an alternative aspect, the microspectrometer can also be configured to operate in the mid infrared electromagnetic region, including radiation in the wavenumber range from approximately 300 $cm^{-1}$ to approximately 4000 $cm^{-1}$. To this end, the analyte detection system can be configured to operate in additional sub-ranges within the wave number bands of 500, 1000, 1500, 2000, 2500, 3000, and 3500 $cm^{-1}$ and any range derived from these values. It should also be understood that for both near infrared and mid infrared analyte measurements, it is not required by the invention that the wavelength range used be a single contiguous range of wavenumbers. For example, in still another aspect, a plurality of different segments of shorted wavenumber ranges can be used, including the combination of wavenumber segments from both the near infrared and mid infrared spectral regions.

Figure 5:
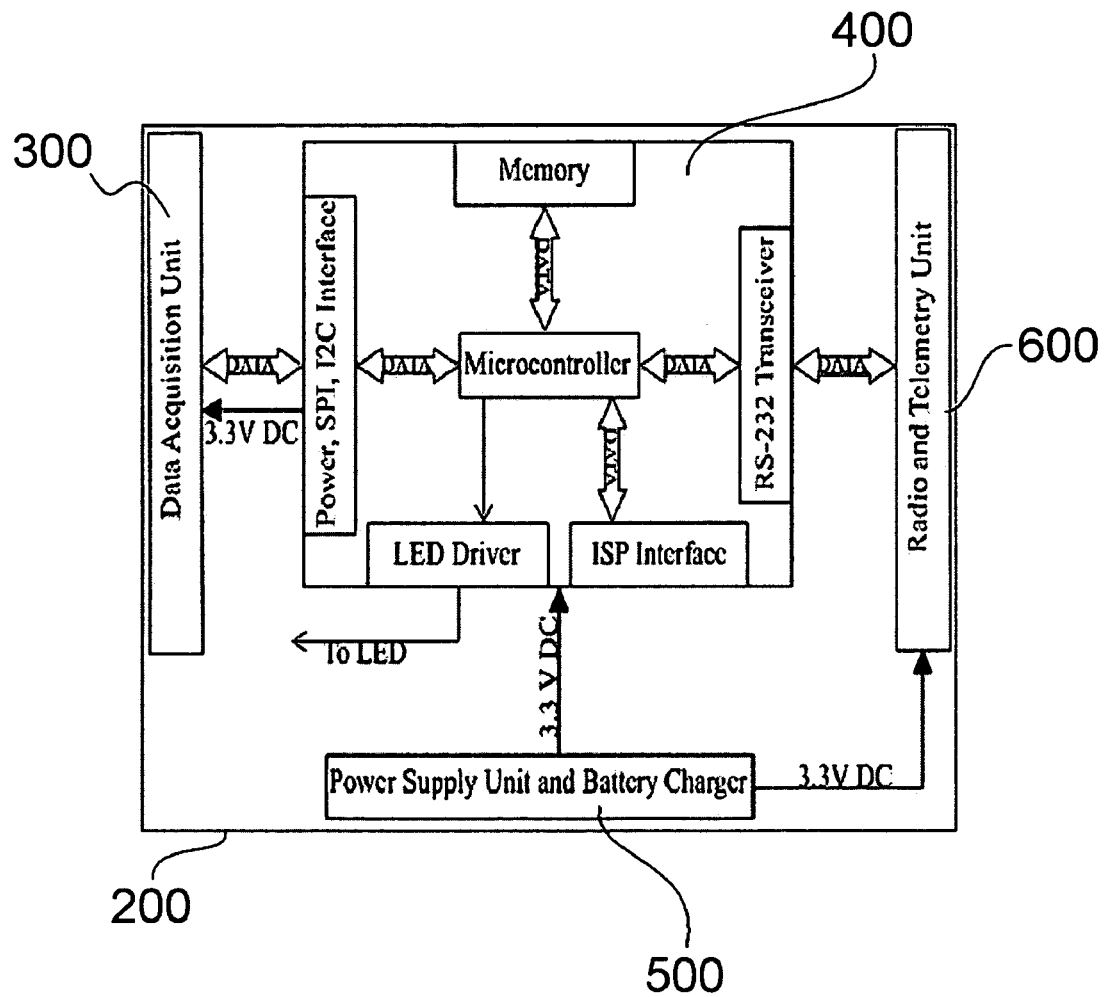
FIG. 5 illustrates a functional block diagram of an exemplary electronic support unit according to one aspect of the present invention.

The desired operational waveband range of the microspectrometer will be dependent, in part, on the particular analyte under investigation. For example, in one aspect where the analyte is glucose, interstitial fluid from the subcutaneous space can be sampled through an embedded filtration probe and subsequently delivered into a micro-fluidic chamber, which is physically isolated from the biological environment. The sample of interstitial fluid can then be carried to an optimized spectrometer cell, where a 16 $cm^{-1}$ resolution near infrared spectrum can be collected over a spectral range of from approximately 4000 $cm^{-1}$ to approximately 5000 $cm^{-1}$ which corresponds to the spectral range containing a spectral signature unique to glucose, as depicted in FIG. 5. Using conventional mathematical models, the concentration of the glucose can be obtained from a direct analysis of the detected glucose absorption spectrum.

As mentioned above, the electromagnetic radiation detector can, in one aspect, comprise a photodiode array configured to detect a desired range or plurality of ranges of electromagnetic radiation. An exemplary photodiode array of the instant invention can comprise an array of solid state p-i-n diodes. To this end, in one aspect, the p-i-n diode can be a reverse biased p-i-n diode. In another aspect, the solid state diodes can be comprised of a semiconductive material suitable for use as a photodetector. For example, and without limitation, a solid state photodiode adapted for use in detecting electromagnetic radiation in the near infrared region can comprise GaInAsSb, InGaAs, PbS, or PbSe. Alternatively, a solid state photodiode adapted for use in detecting electromagnetic radiation in the mid-infrared region can comprise, for example, HgCdZnTe, pyroelectrics, thermopiles, and/or an InAs/GaInSb superlattice material.

In one aspect, a photodetector diode comprising a semiconductive material as described herein can be fabricated by conventional molecular beam epitaxy (MBE). As one of skill in the art will appreciate, MBE is a method of depositing layers of materials with atomic thicknesses on to substrates. This is done by creating a molecular beam of a material which impinges on to the substrate. The resulting superlattices can be suitable for use in semiconducting systems such as the photodetectors described and exemplified herein.

In an exemplary aspect comprising a GaInAsSb p-i-n diode, the light-absorbing "i" layer can, for example, comprise approximately 3 μm of the alloy GaInAsSb. To this end, the GaInAsSb can be grown lattice-matched to a GaSb substrate with a cutoff wavelength for light absorption (depending on alloy composition) ranging from approximately 1.5-4.1 μm at room temperature. In this example, the target band gap for the detector would be approximately 4000 $cm^{-1}$ (2.5 μm), so that the absorption coefficient in the target wavelength range will be approximately 5000 $cm^{-1}$. The absorption length for the above-band gap of light in GaInAsSb alloy can then be approximately 2 μm, so that the majority of the light is absorbed in the "i" layer having the exemplary thickness of approximately 3 μm. As one of skill in the art will appreciate, electron diffusion lengths in such materials can also influence the optimal choice of "i" layer thickness. Further, for these exemplified semiconductive materials, typical mobilities are approximately 3000 $cm^{-2}/Vs$ at room temperature, and typical minority electron lifetimes in highly pure undoped materials are approximately 10 ns. Accordingly, the carriers can diffuse across an "i" layer that is approximately 10 μm thick. To this end, by ensuring that as many created electron-hole pairs will be collected as possible, it will be appreciated that this approach can also maximize the responsivity of the photodetector.

The "p" region of the diode can be comprised of the same semiconductor alloy composition as the "i" layer in order to facilitate collection of the holes. The "n" region can be comprised of slightly larger band gap to eliminate the absorption of the desired wavelength of light. Light absorbed in the "n" region can produce minority holes, which are not particularly mobile, and hence can contribute more to the dark current (and hence noise) than to the signal. Thus, in an exemplary aspect, the "n" region can also be constructed of a relatively thin (0.3 μm) layer of material to further reduce light absorption in this layer and to reduce the dark current.

The responsivity of an electromagnetic radiation detector and/or the presence of dark current can be important considerations when selecting a suitable photodetector for spectroscopic determinations. For example, the response time of a photodetector can be a limiting factor in communication related applications. Additionally, dark current, which is typically the primary noise source intrinsic to a photodetector, can adversely affect the signal to noise ratio of the measurement. To this end, in one aspect, the photodetector array of the instant invention exhibits a signal to noise ratio of approximately 100 μAU for a one-second collection. According to this aspect, the time-averaged noise can be reduced to approximately 5 μAU on the order of 4 minutes. In still another aspect, the time-averaged noise can be in the range of from about 0.1 μAU to about 20 μAU, including such time averaged noise values of 0.5 μAU, 1.0 μAU, 5 μAU, 10 μAU, and 15 μAU.

Detector noise can also be a limitation to achieving high-quality infrared absorption spectra in, for example, the near infrared combination region. Thus, to minimize detector noise and to increase signal to noise ratios, conventional spectrometer systems often utilize liquid nitrogen or multi-stage thermoelectric systems to cool the detector element. However, as one of skill in the art will appreciate, these techniques can in some circumstances be problematic for use with a portable and/or implantable battery-operated system. Thus, in another aspect, the present invention comprises a photodetector that can operate successfully at ambient or body temperatures without the need for a cooling means to control the level of detector noise. For example, in one aspect, a photodetector of the present invention is capable of substantially continuous operation while maintaining a detector temperature less than about 100° F., less than 98° F., less than 95° F., or even less than 90° F.

To this end, the level of noise produced by a detector element is typically proportional to the square root of its surface area. Thus, reducing the size of the detector, provided that the amount of light collected from the light source is held constant, can in one aspect minimize the level of detector noise. Accordingly, in another aspect of the present invention, the impact of detector noise is minimized by reducing the size of the detector assembly while still maintaining a high brightness from the light source. For conventional instruments, the use of a low-brightness, broadband source (such as a tungsten lamp) means that small detector elements are not as practical. However, in the instant invention, by utilizing a high-brightness light source, such as an LED, and taking steps to substantially confine the light in a sub-millimeter optical cell, relatively small detector elements can be used with relatively high responsivity and minimal levels of detector noise.

In still another aspect, the photodetector array of the instant invention can exhibit a specific detectivity (D*) in the range of from approximately of approximately $10^8$ cm $Hz^{1/2}$ watt to approximately $10^{12}$ cm $Hz^{1/2}$ watt, including specific detectivities of $10^9$ cm $Hz^{1/2}$ watt, $10^{10}$ cm $Hz^{1/2}$ watt, and $10^{11}$ cm $Hz^{1/2}$ watt. In one aspect, a photodetector array according to the present invention exhibits a specific detectivity of approximately $10^{10}$ cm $Hz^{1/2}$ watt. As one of ordinary skill in the art will appreciate, the specific detectivity can be calculated using equation (I) set forth below, wherein A is the area of the photosensitive region of the detector, Δf is the effective noise bandwidth and NEP is the noise equivalent power.

$$D^* = \frac{\sqrt{A\Delta f}}{NEP}, \qquad (I)$$

In one exemplary and non-limiting aspect, the area A of the photosensitive region of the detector array can be in the range of from approximately 0.4 mm×50 μm to approximately 3 mm×100 μm. In another exemplary and non-limiting aspect, the area of the photosensitive region of the detector array can be 1 mm×50 μm. Likewise, in one exemplary and non-limiting aspect, the NEP/$\sqrt{\Delta f}$ can be in the range from approximately 10 fW/$Hz^{1/2}$ to approximately 10 pW/$Hz^{1/2}$.

A stated above, a spatially variable bandpass filter can be mounted on the photodiode array. The filter can be configured such that the central wavelength of the passband varies along one of the dimensions of the filter. For example, a filter can have a passband width in the range of from 12 $cm^{-1}$ to 20 $cm^{-1}$. Still further, in a configuration adapted for the analysis of glucose in interstitial fluid, a filter can have passband width of 16 $cm^{-1}$. Thus, it will be appreciated that by using a bandpass filter, each photodetector element, or photodiode, can be adapted to be sensitive to a different wavelength of light. An exemplary spatially variable filter is the JDSU LVF 14002500-3 and is commercially available from Optical Coating Laboratory, Inc.

The electromagnetic radiation source can, in one aspect, comprise any conventional light source capable of providing electromagnetic radiation in the waveband region corresponding to the spectral features of an analyte under investigation. In one aspect, and as mentioned above, the light source can be a high efficiency broad band LED. The LED can, for example, be comprised of GaInAsSb and based on a similar p-i-n semiconductor structure as described in connection with the exemplary photodiode elements discussed above. In an alternative aspect, the LED can comprise an InAs/GaInSb super lattice. Similar to the fabrication of the photodiode described above, an LED according to the present invention can also be fabricated using conventional molecular beam epitaxy.

Although LEDs can be very efficient light sources as compared with Globars or tungsten lamps, the LED can also have the largest power draw of any component in the system. This can mean that the efficiency of the LED can dominate the operation time available from a single battery. For example, a typical LED voltage requirement can be approximately 0.7 V and the typical current draw can be approximately 140 mA. Further, these values can, in one aspect, be mismatched with the corresponding voltage and current values associated with a typical portable battery source as well as the other optional electronics components (~5 V and <10 mA) that will be described in detail in connection with the electronic support unit.

To this end, in one aspect, the present invention further comprises a high efficiency LED assembly that can minimize or eliminate the mismatch in current and voltage discussed above. A conventional LED typically incorporates a single emitting layer in the center of a p-i-n diode junction. However, in a cascaded system, several p-i-n junctions can be cascaded in series within a single LED active region using, for example, Esaki tunnel junctions. Using a cascade of, for example, 5 emitter regions can therefore increase the voltage requirement of the light source and decrease the current draw by a factor of 5. Thus, using the typical exemplified voltage and current values discussed above, active cascading of 5 emitters can, for example, provide a light source having a net voltage requirement of 3.5V and total current draw of approximately 28 mA without altering the output optical power of the light source. As one of skill in the art will appreciate, this can, in one aspect, significantly extend battery life, which can be particularly well suited for use with portable, continuous and/or implantable analyte detection systems. Accordingly, in view of the foregoing description, one of skill in the art will be able to readily determine the desired level of LED cascading needed to optimize the efficiency of a light source in a given system without requiring undue experimentation. In still another aspect, it is envisioned that the light source can comprise a tunable laser diode.

The microspectrometer further comprises an optical sampling cell having a cell housing that defines a fluid inlet port and a fluid outlet port, wherein the fluid inlet port can be configured to receive an optical sampling fluid from a test subject. Still further, in another aspect, the fluid inlet port can be adapted to continuously receive sampled fluid, such as an interstitial fluid, from a sampling assembly. In one aspect, the electromagnetic radiation source and the electromagnetic radiation detector can be aligned with the optical sampling cell such that the sampling fluid delivered to the optical cell can be irradiated with a desired waveband of electromagnetic radiation and so the detector can subsequently detect variations in the electromagnetic radiation resulting from the interface of the electromagnetic radiation with the interstitial fluid.

The desired geometry for the optical cell can depend, in part, upon the particular flow dynamics within the analyte detection system as well as the optical configuration of the light source and photodetector assembly. To this end, the desired optical cell geometry can be readily derived and/or optimized by one of ordinary skill in the art without requiring any undue experimentation. However, in one aspect, and as exemplified herein without limitation, an optical cell can be substantially cylindrical in shape, comprising a diameter of approximately 200 µm, an optical path of approximately 1 mm and an interior volume of approximately 31 nL. In an alternative aspect, the optical sampling cell or chamber can be substantially rectangular, such as for example, the cell provide by a square capillary member. According to this aspect, a light source such as an LED can be mounted directly on one wall of the capillary and the detector assembly can be mounted directly on to the opposing wall of the capillary member.

In another aspect, the optical cell can be configured to provide a substantially laminar flow. To this end, one of ordinary skill in the art will appreciate that a substantially laminar flow within the optical cell can minimize the residence time of an interstitial fluid sample delivered to the optical cell. Minimizing residence time can therefore reduce the lag time within the detection system. For example, the vast majority of interstitial fluid volume present within the detection system at any given time can be in the optical cell region. Thus, in the exemplified aspect where the optical cell has a diameter of approximately 200 µm and has an interior volume of approximately 31 nL, if laminar flow conditions are achieved at a flow rate of approximately 100 nl/min, the approximate time needed to replace substantially all of the fluid in the optical cell will be less than approximately 20 seconds. To this end, it will be appreciated that higher and lower flow rates can also be used with the present invention. For example, and without limitation, a suitable flow rate can be in the range of from approximately 30 nl/min to approximately 150 nl/min.

In still another aspect, the interior walls of the optical cell may be coated or metalized in order to maximize electromagnetic radiation throughput through the optical cell. This could, for example, be accomplished by photolithography using a conventional bi-level resist lift off scheme.

In still another aspect, and as further shown in FIG. 2, the optical cell 122 can be fabricated in a microfluidic chamber 180 having a micro fluidic inlet channel 182 and a micro fluidic outlet channel 184. As depicted, the inlet channel can be in fluid communication with a sampling assembly and the outlet channel can be in fluid communication with a vacuum source such that interstitial fluid can be drawn into the sampling assembly and propagated through the optical sampling cell.

The microfluidic chamber can be fabricated from a single substrate material using conventional means such as laser micromachining, chemical etching, diamond drilling, and/or ultrasonic drilling. In still another aspect, the microfluidic assembly can be molded from any suitable infrared transmitting polymer. For example, in one aspect, and without limitation, an infra red transmitting fluoropolymer such as TEFLON AF, commercially available from Dupont, can be used to mold a microfluidic chamber according to the instant invention. As one of skill in the art will appreciate, TEFLON AF is transparent to certain wavebands of infrared radiation and has an index of refraction that is less than that of water or ISF. Thus, TEFLON AF or any similar polymer can in another aspect also serve as a waveguide for the IR radiation. To this end, the manufacturing flexibility offered by the fabrication strategies and materials set forth above can provide the added ability to customize the geometry of the optical cell to virtually any desired specifications.

Microfluidic tubes from the sampling assembly and vacuum source can, in one aspect, be coupled to the microfluidic chamber by fitting the tubing into, for example, a microfabricated recess in the distal ends of the inlet and outlet channels. The tubing can be secured, for example, using a UV curable silicone, commonly used in medical device fabrication. In another aspect, the attachment of the sampling assembly lead to the optical cell can be accomplished using commercially available, low dead volume connectors. In another aspect, the entire microfluidic chamber unit can be closed by affixing infrared transmitting windows to the top and bottom of the chamber using any conventional adhesive, such as a uv photocurable adhesive. It should be understood that the size of the microfluidic chamber can be scaled up or down to any desired dimension. In one aspect, the optimal size of the micro fluidic chamber can depend on, for example, the structural strength needed to prevent breakage of the connection points to the ultrafiltration inlet and outlet lines.

Figure 4:
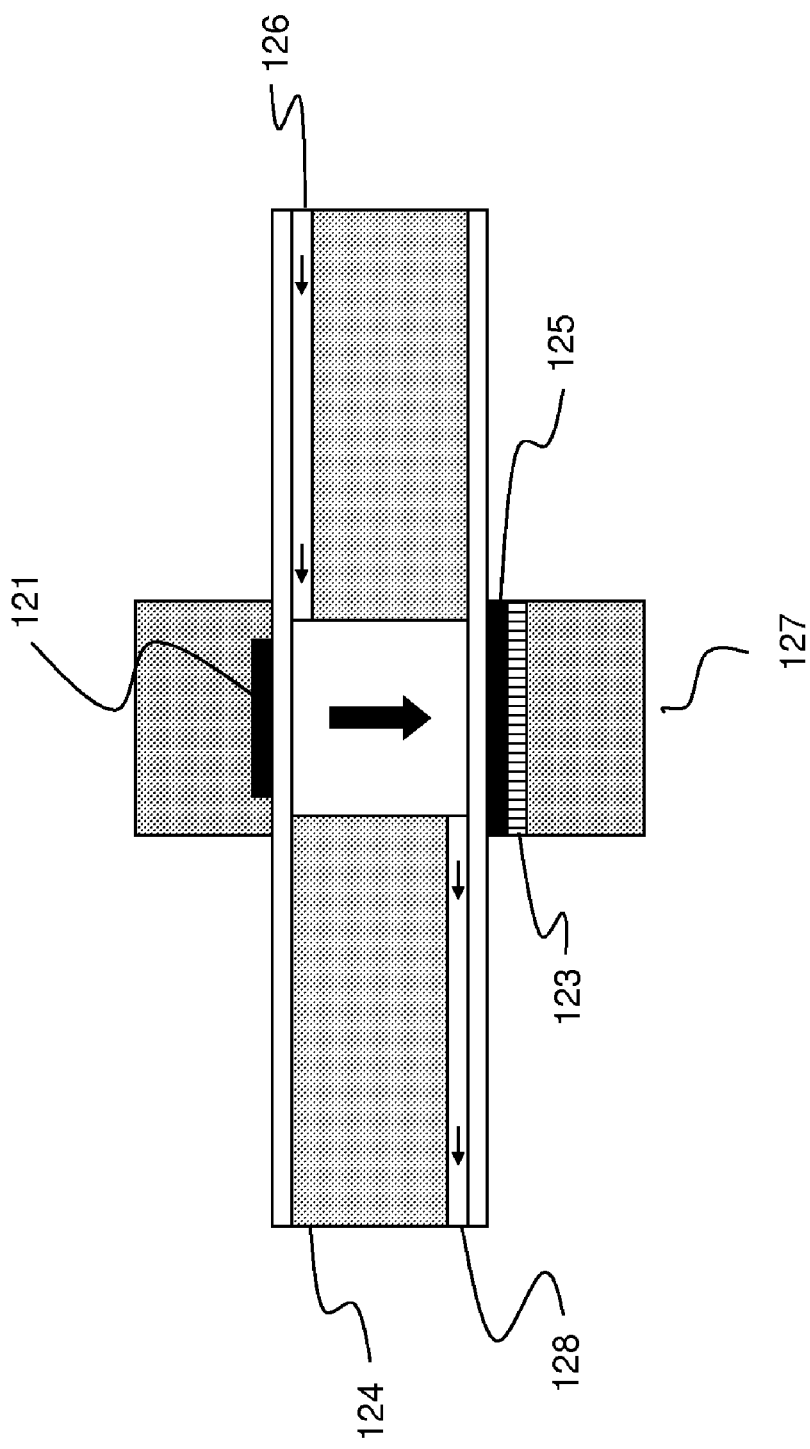
FIG. 4 illustrates a side view of a microspectrometer according to one aspect of the present invention.

As illustrated in FIG. 4, the electromagnetic radiation source 121 and detector assembly 127, mounted on respective headers, can be aligned with the optical sampling chamber and affixed or connected directly to a microfluidic chamber with, for example, a photo curable adhesive. The components can, for example, be bonded to the microfluidic chamber substrate using anodic bonding to ensure a long lasting hermetic seal for the main assembly. Electrical connections from the source and detector can be supplied by, for example, by flexible ribbon cables that can be affixed to metallic (i.e. gold) pads on the headers. The ribbon cable can then be attached to the system control electronics discussed in detail below. This entire assembly can, in another aspect, be potted in a photocurable medical grade RTV silicone, which can protect the assembly from shock and ensure protection from the surrounding environment. It can also provide temperature insulation so that the system can operate under a relatively stable operating temperature profile. Further, according to this aspect, it will be appreciated that the source radiation does not emerge into air and can therefore maintain the brightness advantage associate with the higher refractive indices associated with the interstitial fluid.

The analyte detection system further comprises a sampling assembly for obtaining a sample fluid, such as interstitial fluid. The sampling assembly can be positioned in fluid communication with the optical sampling cell of the microspectrometer via any conventional commercially available microfluidic tubing and connectors. In one aspect, the microfluidic tubing connecting the sampling assembly to the optical cell can be constructed and arranged to minimize the amount of dead volume within the system. To this end, one of ordinary skill in the art will appreciate that having the optical cell positioned relatively close to the sampling assembly can minimize the amount of dead volume within the system and significantly decrease the lag time in analyte measurements. In one aspect, sampling lag times of less than 60 seconds can be achieved utilizing only a few centimeters of tubing between the sampling assembly and the optical cell.

As one of skill in the art will appreciate, there are a variety of conventional techniques that can be used to access interstitial fluid from a test subject, including, for example, the implantation of subcutaneous sampling probes, extraction of interstitial fluid through intact skin by electrical current, drawing interstitial fluid out of the skin with a micro-cannula, insertion of a microdialysis probe into the skin, insertion of an ultrafiltration probe into the skin and the use of an implanted wick. The sampling assembly of the instant invention can comprise any one or more of these or any other conventional technique for obtaining a sample of interstitial fluid from a test subject.

In two exemplary and non-limiting aspects, microdialysis and ultrafiltration can be used in the instant invention as an effective means for sampling interstitial fluid. Both microdialysis and ultra-filtration involve mass transport of an analyte of interest across a conventional semi-permeable membrane that can be implanted in the subcutaneous tissue of a test subject. Because of the typical hydrophobicity and molecular weight limits of conventional semi-permeable membranes, these techniques can be well suited for sampling hydrophilic substances (i.e., interstitial fluid) and can provide samples that are substantially free of extraneous proteins (enzymes), cells and/or other large molecular weight substances.

In conventional microdialysis sampling, the sampling assembly can comprise an access probe that is implanted into subcutaneous tissue. The probe comprises a semi-permeable membrane. In use, the semi-permeable membrane is perfused with a physiological solution. Water soluble substances in the interstitial fluid (ISF) can consequently diffuse across the semi permeable dialysis membrane and enter the perfusate, which can then be analyzed by the microspectrometer. With this technique, substances in the ISF can be monitored and, for example, the effects of locally delivered drugs can be studied.

The driving force for the diffusion of the analyte from the tissue and across the membrane wall is, in one aspect, the concentration gradient of the particular analyte of interest in the interstitial fluid relative to the perfusate. Typically, the perfusate is selected to be iso-osmotic with the surrounding tissue, the hydrostatic pressure is relatively minimal and there is no net fluid transfer between the perfusate and the tissue. To this end, additional techniques such as no-net flux and retrograde dialysis can also be used to ensure the exact determination of analyte concentrations. As one of ordinary skill in the art will appreciate upon practicing the present invention, in another aspect it may be desirable to utilize conventional ultra-slow microdialyis.

It should be understood that particular aspects and parameters of a suitable microdialysis assembly, such as the desired flow rate, the composition of the semi-permeable membrane, and the composition of the perfusate, will be dependent, in part, upon the particular analyte under investigation and fluid dynamics of the analyte detection system. These particular parameters can be optimized by one of ordinary skill in the art without the need for any undue experimentation. To that end, exemplary and conventional microdialysis systems and methods that can be used with the instant invention are disclosed and described by Rooyackers O., Thorell A., Nygren J., Ljungqvist O. Microdialysis Methods for Measuring Human Metabolism *Current Opinion in Clinical Nutrition & Metabolic Care.* 7(5):515-21, 2004 and by Chaurasia C S. In vivo microdialysis sampling: theory and applications. *Biomedical Chromatography.* 13(5):317-32, 1999, the entire disclosures of which are hereby incorporated by reference in their entirety for all purposes As stated above, in another aspect, the sampling assembly can comprise a conventional ultra-filtration system. To this end, ultra-filtration similarly utilizes an implantable semi-permeable membrane. However, ultra-filtration does not typically involve the use of a perfusate, but, instead relies on a pressure differential applied across the semi-permeable membrane as the driving force for the extraction of an analyte-containing sample of interstitial fluid. Typically, the pressure differential is supplied in the form of a vacuum source. The reduced pressure provided by the vacuum source results in a hydrodynamic flux across the membrane, with water and one or more permeable solutes also being extracted from the tissue surrounding the membrane. As one of skill in the art will appreciate, ISF is rapidly replenished and the amount of fluid being sampled is small relative the entire pool of ISF available for sampling. Thus, in accordance with this aspect, ultra-filtration can be particularly well suited for use in a sampling assembly constructed and arranged for extended and continuous removal of ISF. Furthermore, conventional microdialysis typically involves the need to recalibrate the system periodically in order to account for changes in the diffusion properties of molecules across the membrane. In contrast, it will be appreciated upon practicing the present invention that ultra-filtration does not require periodic recalibration of the analytical system periodically in order to account for changes in the diffusion properties of molecules across the ultra-filtration membrane.

Any conventional vacuum source can be used in connection with a sampling assembly of the instant invention. Examples of suitable vacuum sources include, without limitation, an evacuated vial or vacutainer, a monovette, portable battery powered syringe pumps, and micro syringe pump systems. In one aspect, power for a battery powered pump unit can be controlled and supplied by the ESU described herein. The vacuum source can be used to draw the ISF across the ultrafiltration membrane. In one aspect, the vacuum source will be able to provide a flow rate in the range of from 30 nl/min to 150 nl/min. In another aspect, the vacuum source will be able to draw interstitial fluid at a flow rate of approximately 100 nl/min. To this end, it should be understood that the desired flow rate in microdialysis and/or ultrafiltration can also depend, in part, upon the configuration of the microfluidic chamber, dimensions of the probe and the level of negative pressure provided by the vacuum source.

As one of skill in the art will also appreciate, bubble formation within the sampled interstitial fluid can occur during the filtration process and can result in an inaccurate optical analysis of the sampled ISF. This typically results as a function of the negative pressure, with bubble formation increasing proportional to an increase in pressure. Further, bubble formation can also result as a function of increased flow rate. Thus, in another aspect, it should be understood that minimization of bubble formation in the sampled ISF can be obtained by optimizing pressure and flow rate of the interstitial fluid through the sampling probe and subsequently through the micro-fluidic chamber such that bubble formation is minimized. To this end, one of ordinary skill in the art will be able to arrive at such optimized conditions without the need for undue experimentation.

In an exemplary aspect where glucose is the analyte under investigation, the sampling assembly is comprised of an ultra-filtration probe such as the BAS UF-312 ultra-filtration probe commercially available from Bioanalytical Systems. This exemplary ultra-filtration probe is made from a polyacrylonitrile membrane and has an outer diameter of approximately 320 um and membrane wall thickness of approximately 50 um. As will be appreciated by one of skill in the art, prior to implantation, the probe can be sterilized with, for example, ethylene oxide. The exemplified probe can then be implanted anywhere on the body having a soft tissue layer sufficiently thick to accommodate the protrusion of the access port into the subdermal space. In one aspect, the implant can be placed on the wrist or arm area for easy patient access and may include a device or implement to cover the port such as a wrist watch interface or skin colored bandage to improve patient acceptance of the aesthetic qualities of the device. Further, for durability, the access port can in another aspect be placed somewhere on the body that is not subject to a lot of exposure or contact such as the abdomen.

It will be appreciated in view of the foregoing description that an implantable ISF access probe can provide a method for withdrawal of body fluids without requiring further breach of the skin barrier. The implantable access probe can also provide for filtration of interstitial fluid, thereby resulting in a sample of fluid containing an analyte of interest and substantially free of extraneous proteins and/or cells. In another aspect, because of its porosity and fibrous structure, the implanted access port can form an infection-free, transcutaneous implant having a biological seal around the device. Therefore, the implant can be suitable for long term use. Further, since the implant can reside in the plane between the subcutaneous and dermal layers of tissue, subsequent removal can be relatively simple if necessary.

The direct in situ sampling of interstitial fluid can in one aspect simplify the task of detecting an analyte as compared to other conventional non-invasive measurement approaches that rely on detecting an analyte based on spectral data obtained from a more complex and/or heterogeneous skin matrix. More specifically, interstitial fluid is typically a clear fluid with relatively few or even no scattering particles (such as cells), and thus the optical throughput can be orders of magnitude higher than transmission measurements through skin or whole blood. Further, because the optical geometry of the method set forth above can be defined by the path length of the sampling chamber, the interpretation of measured spectra in terms of absolute analyte content can also be much more straightforward compared to methods that rely on diffuse reflection, transflection, or photoacoustic arrangements.

One of skill in the art will appreciate that a microspectrometer as described and exemplified herein does not require the use of moving parts and/or imaging optics and can therefore occupy a relatively small volume of space. Thus, in one aspect, microspectrometer according to the present invention can occupy as small or as large a volume as is desired. For example, the microspectrometer can occupy a volume as small as the technology of the individual components themselves will allow. In one aspect, and without limitation, a microspectrometer according to the present invention can occupy a volume in the range of from approximately 0.01 $cm^3$ to approximately 1.0 $cm^3$, including volumes of 0.02 $cm^3$, 0.03 $cm^3$, 0.04 $cm^3$, 0.05 $cm^3$, 0.06 $cm^3$, 0.07 $cm^3$, 0.08 $cm^3$, 0.09 $cm^3$, 0.1 $cm^3$, 0.2 $cm^3$, 0.3 $cm^3$, 0.4 $cm^3$, 0.5 $cm^3$, 0.6 $cm^3$, 0.7 $cm^3$, 0.8 $cm^3$, 0.9 $cm^3$, and any range derived from these values. In still another aspect, the microspectrometer can occupy a volume that does not exceed approximately 0.1 $cm^3$.

In still another aspect, the present invention provides a method for the reagentless optical detection of an analyte in a fluid sample. The method can generally comprises providing an analyte detection system as described herein, comprising: (i) an optical sampling cell having a cell housing defining a fluid inlet port and a fluid outlet port, the fluid inlet port; (ii) an electromagnetic radiation source in communication with a first portion of the optical sampling cell housing; and (iii) an electromagnetic radiation detector in communication with a second portion of the optical sampling cell housing. A fluid sample containing an analyte can be obtained from a test subject and conveyed through the inlet port in to the optical sampling cell. Electromagnetic radiation generated by the electromagnetic radiation source can irradiate at least a portion of the fluid sample within the optical sampling cell and the electromagnetic radiation detector can optically detect electromagnetic radiation emanating from the optical sampling cell. Still further, if desired, at least a portion of the obtained fluid sample contained within the optical sampling cell can be returned to the source of the sample fluid, such as the test subject.

It should also be understood that the reagentless optical analyte sensor and method of the instant invention can also be used in a variety of applications. For example, as exemplified herein, the analyte sensor can be used to monitor the presence and concentration of one or more analytes in the interstitial fluid of a test subject. To this end, the microspectrometer can be used to spectroscopically analyze interstitial fluid in either an in-vivo configuration or, alternatively, in an ex-vivo configuration.

In an in-vivo configuration, the microspectrometer can be implanted in the subcutaneous tissue of the test subject. The subcutaneously implanted sampling assembly probe can continually draw a small volume of interstitial fluid (ISF) from the test subject and pass the stream of ISF through the optical sampling cell where it can be analyzed spectroscopically for any number of targeted analytes. By providing a reagentless optical analyte sensor, the lack of reaction byproducts enables the sample fluid to then be returned to the body of the test subject without concern of contamination or poisoning. In one aspect, it is also envisioned that a microspectrometer could be placed in the peritoneal cavity of a test subject and the sampling assembly probe can be imbedded in the subcutaneous tissue bed surrounding the peritoneal cavity.

Alternatively, in an ex-vivo configuration, a sampling assembly probe can be implanted subcutaneously and can again continuously draw a relatively small sample volume of interstitial fluid (ISF) from the test subject and pass the stream of ISF through the optical sampling cell of a microspectrometer where it can be analyzed spectroscopically for any number of targeted analytes. In accordance with this configuration, the microspectrometer can be positioned external to the test subject, such as for example, by being affixed to or worn on the surface or skin of a test subject. By virtue of the microspectrometer being a reagentless optical analyte detector, even in an ex-vivo arrangement the sample can, if desired, be returned back to the subcutaneous tissue of the test subject. Alternatively, due to a potential fear of infection, the sample fluid obtained from an ex-vivo arrangement can also be externally collected and disposed. To this end, in an exemplary aspect where the sampling flow rate is approximately 150 nL/min, the system would generate approximately 216 microliters per day that could be externally collected and disposed of.

To this end, the reagentless optical analyte sensor can in one aspect be integrated into a nocturnal glucose monitoring system. In another aspect, the analyte sensor can be used in connection with a closed loop automated biological delivery system, such as an artificial pancreas adapted to selectively deliver insulin to a test subject.

In still another aspect, the analyte sensor can be used to spectroscopically analyze sample fluids other than interstitial fluids. For example, the analyte sensor can be used in connection with traditional clinical analysis of biological fluids such as blood and/or urine. Thus, in one aspect, the analyte sensor can be used to enable the real-time optimization of hemodialysis treatments by monitoring analytes such as urea, lactate, creatinine, phosphate, and/or sulfate present within the blood of a test subject undergoing hemodialysis treatment. In an alternative aspect, the reagentless optical analyte sensor can also be used in connection with general blood chemistry, where, for example, the analyte sensor can be used to monitor the presence and concentration of one or more analytes in the blood of test subject.

In still another application, the reagentless optical analyte sensor of the instant invention can be used to monitor process chemistry. For example, and without limitation, the reagentless optical analyte sensor can be used on connection with a bioreactor to monitor the level of nutrients and/or cellular waste products to maximize growth. Additionally, the analyte sensor can be used to monitor industrial chemical processes and or environmental process monitoring.

As briefly stated above, in another aspect the present invention provides a an electronic support unit (ESU), for use in connection with a reagentless optical analyte detection system as described above. In one aspect the controller or electronic support unit is in communication with an analyte detection system and can enable the continuous and reagent-free optical analysis of interstitial fluid (ISF) present within a test subject. To this end, in one aspect, the controller can provide a physical interface between one or more optical sensing elements designed to obtained analyte related data.

An electronic support system 200 according to the instant invention can be constructed and arranged so as to comprise a battery powered primary or internal module that can be affixed to a test subject and an external or remote module that can be positioned in a remote location a predetermined distance from the internal module. In one aspect, the primary or internal module can be optionally implanted in the subcutaneous tissue of a test subject. In an alternative aspect, the primary or internal module can be affixed to or worn on a surface of the test subject. For example, and without limitation, the primary module can be releasably affixed to or worn on the skin of a human test subject.

The electronic support system 200 can, in one aspect, enable continuous operation of a biological data sensor for extended durations with relatively minimal or even no user intervention. Further, the electronic support system 200 can operate from a battery based power supply capable of remote charging. To this end, the electronic support system 200 as configured and described herein can further operate at relatively low power supply voltages such as, for example, 3.3 volts. Such a power supply can provide continuous energy for up to and even exceeding 24 hours of system operability.

The primary or internal module comprises a data acquisition unit (DAU), a main controller unit (MCU) comprised of a dedicated microcontroller unit to control the sensor system; an internal power unit (IPU) to supply power to one or more of the components in the internal module, and a first telemetry unit (TU) for communicating analyte related data to the external or remote module. The external module can comprise a remote charger unit (RCU) that can transmit inductive power to the internal power unit, and a second telemetry unit that can receive sampled data that has been transmitted from the first telemetry unit of the internal module. Functionally, the ESU 200 in one aspect is therefor comprised of a Data Acquisition Unit (DAU) 300, Main Controller Unit (MCU) 400, Power Supply Unit (PSU) 500, and the Telemetry Unit (TU) 600 respectively, as shown in FIG. 5.

The main controller unit or MCU 400 can, in one aspect, provide one or more functions including, without limitation, obtaining sampled analyte data from the data acquisition unit, storing the obtained data in memory, packaging the data along with a time stamp, and/or subsequently transmitting the data through the telemetry unit (TU) 600. The main controller can also be responsible for coordinating the communication between the internal and external modules and ensuring proper operation of one or more units within the system.

Figure 6:
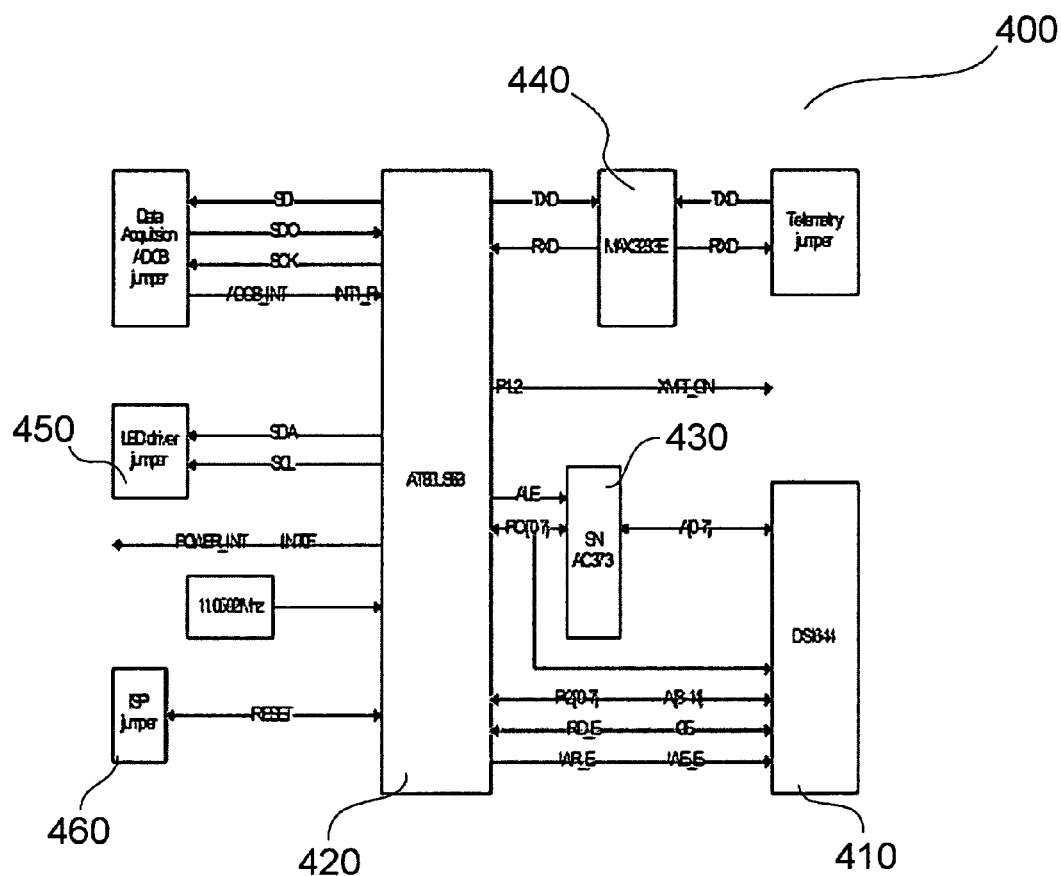
FIG. 6 is a schematic of an exemplary main controller unit according to one aspect of the present invention.

An exemplary schematic of an MCU 400 according to the instant invention is illustrated in FIG. 6. As depicted, the MCU comprises a memory component 410 and a microcontroller component 420. While any conventional memory device can be used with the MCU, the commercially available Dallas Semiconductor DS1644 NVRAM memory, equipped with a real time clock (ETC) and back-up Li-ion battery can be used for data storage in an exemplary aspect. As one of skill in the art will appreciate, the NVRAM with an integrated circuit can provide fast access to data and a real time clock for time-stamping the data. Further, the memory and real time clock combination can, in one aspect, eliminate the need for additional time keeping hardware. An alternative memory device which is suitable for use in the instant invention can be the Ramtron FM31256 32 KB FRAM memory, also equipped with a real time clock. The FRAM can offer virtually unlimited read/write cycles, relatively fast access to data, and as mentioned, a real time clock for time stamping the data.

In one aspect, it is desired for the memory capacity to be sufficient to store up to approximately 24 hours of sampled data. According to this aspect, at an exemplary sampling rate of one sample every 5 minutes and approximately 3 bytes of memory needed per sample per channel, an additional 6 bytes per sample for timestamp and error detection, a data memory capacity of at least 29.4 KB can be needed to store 24 hours of data obtained from a 32 photodiode array. To this end, one of skill in the art can appreciate that any desired memory capacity can be used in the instant invention and further, the desired memory capacity can be calculated according to the following equation:

$$\text{Memory Capacity} = d \cdot R \cdot S \cdot n$$

where d is the duration in hours, R is the sampling rate in samples per hour; S is the sample size in bytes per channel per sample, n is the number of channels.

To enable data collection, light source control, data processing, and/or operation of the telemetry generation, a microcontroller 420 is incorporated into the Main Control Unit. According to this aspect, since the microcontroller can in one aspect be accessing data stored in external memory, a microcontroller that supports external memory can be used. To this end, as one of ordinary skill in the art will appreciate, it can also be desired, although not required, for a single microcontroller unit to support one or more of the other instrumental requirements, while maintaining as small of a size as possible with as low power consumption as possible.

In still another aspect, it can be further desired, although it is not required, for the microcontroller to comprise an instruction set supporting multiplication and division instructions such that it is capable of performing floating point operations. Additionally, a suitable microcontroller can comprise either an internal program flash or an external flash memory. Any conventional and commercially available microcontroller capable of performing one or more feature set forth above can be used in accordance with the present invention. However, the specific features described above can typically be provided in an exemplary conventional 8-bit microcontroller such as those tested and indicated in Table 1 below. While any one of the microcontrollers listed in Table 1 is suitable for use in the instant invention, a comparison of these four commercially available 8-bit microcontrollers indicates that in one aspect, a suitable microcontroller for use in the Main Controller Unit is the Atmel AT89C51ID2.

TABLE 1

| | Exemplary Microcontrollers | | | |
|---|---|---|---|---|
| Features | AT89LS53 | ATtiny26L | MC68HC805 | AT89C51ID2 |
| Architecture | 8051 | AVR | 68 | 8051 |
| Supply Voltage | 2.7 V | 2.7 V | 5 V | 3.3 V |
| Program Memory | 12 kB | 2 kB | 8 kB | 64 kB |
| RAM (bytes) | 256 | 128 | 192 | 2048 |
| IO Pins | 32 | 16 | 20 | 32 |
| Clock Speed (Max) | 12 MHz | 16 MHz | 4 MHz | 160 MHz |
| ISP | Yes | Yes | No | Yes |
| MUL, DIV Inst | Yes | No | No | Yes |
| Interrupts | 9 | 11 | 10 | 9 |
| Timers | 3, 16-bit | 2, 8-bit | 16-bit, 8-bit | 3, 16-bit |
| UART Module | Yes | No | No | No |
| SPI Module | Yes | No | No | No |

In still another aspect, a suitable microcontroller can typically supply multiplexed address-data lines. Thus, in order to access the external memory, a transparent octal D-type latch 430 with tri-state outputs can be used. To this end, a suitable latch for the multiplexing can, in one aspect, have a latch switching delay that is negligible as compared to the memory access time, which is typically of the order of 120 ns for the DS1644 NVRAM memory described above. An exemplary D-type latch that is suitable for use in the instant invention is the Texas Instrument SN74AC373 octal D-type latch with a switching delay of approximately 15 ns.

The microcontroller unit is also provided with a telemetry unit interface 440 to interface the telemetry unit with the main controller. The telemetry unit interface can be any communication interface such as, for example, USB, serial, firewire, parallel, and the like In one aspect, the telemetry unit interface can comprise an RS-232 serial port. The RS-232 serial port can provide added debugging functionality as well. Virtually any conventional and commercially available RS-232 serial port can be used to provide the telemetry interface. While any transceiver known in the art can be used, in one aspect, a suitable RS-232 transceiver can provide true RS-232 signal levels with minimum board space, low power consumption, and suitable operating voltage. To this end, the Maxim MAX3233EWE dual RS-232 transceiver with internal charge pumps is a non-limiting example of a RS-232 transceiver that is suitable for use in the instant invention. The MAX3233E can operate in the voltage range of 3.0-3.6V DC with 1 uA supply current. Additionally, the MAX3233E is capable of entering into a sleep mode when either the RS-232 cable is disconnected or when the UART driving the transmitter inputs is inactive for more than 30 seconds. From the sleep mode, the MAX3233E can turn on again when it senses a valid transition at any transmitter or receiver input. As one of skill in the art will appreciate, this feature can help to conserve power in the system.

The microcontroller can further comprise one or more peripheral support interfaces such as, for example, a jumper for a light source connector 450, an ISP jumper 460, and other serial interfaces to facilitate connectivity of other controller modules and/or other system components.

As stated above, the electronic support system further comprises a data acquisition unit (DAU) 300 that can obtain sampled data from a biological data sensor, such as for example, data detected by the optical sensing component of an analyte sensor. In one aspect, the data acquisition unit can obtain data in a first format and can transform that sample data into a second format. For example, the DAU 300 can obtain sampled voltage data from a photodiode array in an analog format and can transform the analog data into digital format having a predetermined level of precision.

Figure 7:
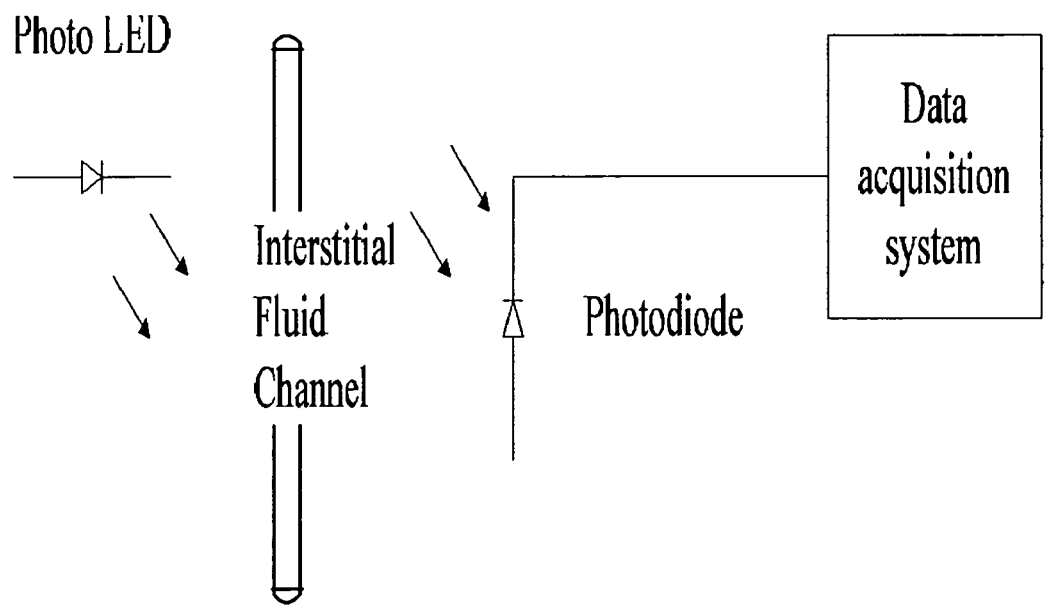
FIG. 7 illustrates an exemplary data acquisition from one photodiode of the photodiode array depicted in FIG. 3.

In one aspect, the data acquisition unit (DAU) 300 can comprise a current integrator and an analog/digital (A/D) converter. The A/D converter can be interfaced to the main controller unit through any conventional interface, such as for example a serial peripheral interface (SPI). The level of precision for A/D conversion can vary as desired and can in one aspect be in the range of from at least 8 bits up to and even exceeding 128 bits, including additional precision values of 16, 20, 24, 32, 64 and any range derived from these values. In another aspect, the precision for the A/D converter is at least 20 bits. The data obtained can be transmitted to the MCU 400 through an SPI interface, where they can be stored in memory and subsequently transmitted through the first telemetry unit interface to the remote telemetry unit for analysis of the particular analyte levels. Thus, in the above-exemplified glucose sensor, the DAU can, for example, perform the task of sampling the photo diode currents from the 32 photodiodes depicted in FIG. 3. The 32 photodiode array provides 32 channels of the optical sensor, with each channel corresponding to different regions in an NIR spectrum. The DAU 300 can also convert the 32 channels into high precision voltage values, such as for example, 16, 20, or even 24 bit voltage values. An exemplary data acquisition from one photodiode of the 32 photodiode array is illustrated in FIG. 7.

Figure 3:
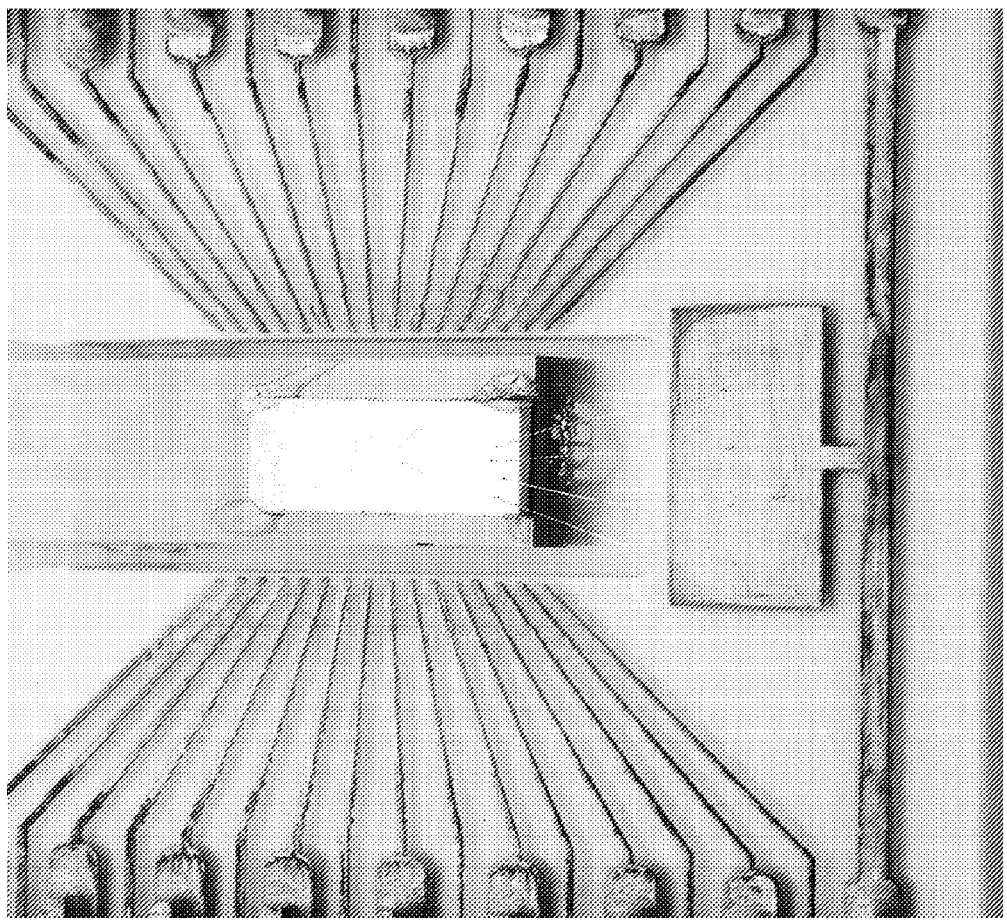
FIG. 3 illustrates an optical sensing element according to one aspect of the invention. As depicted, the optical sensing element comprises an array of 32 photodiodes.
Figure 8:
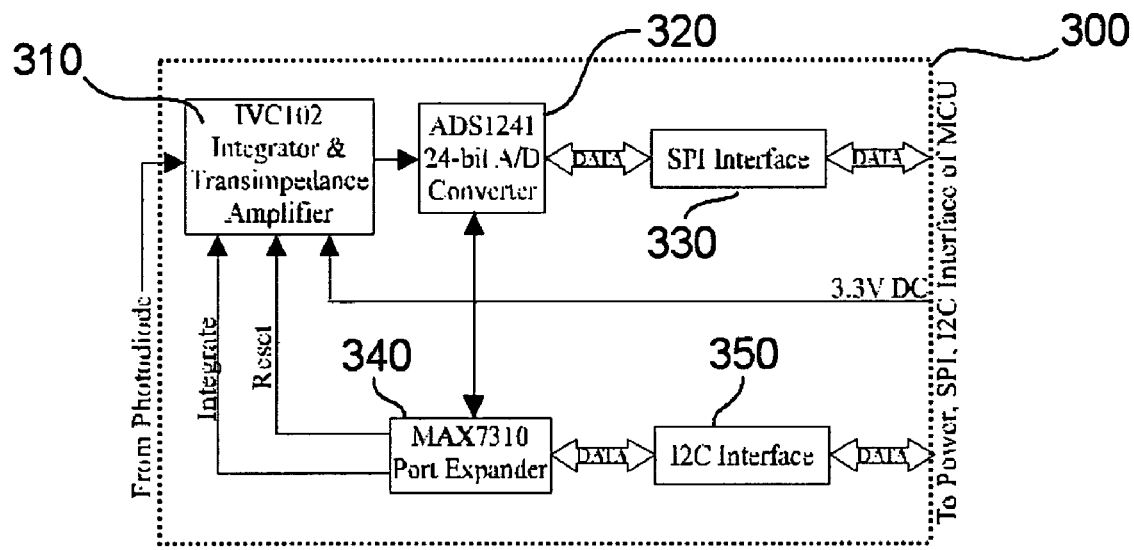
FIG. 8 is an exemplary schematic of a data acquisition unit according to one aspects of the present invention.

FIG. 8 illustrates an exemplary schematic diagram of a data acquisition unit 300 for one channel of a photo diode. As shown, the data acquisition unit comprises a current integrator 310, such as the IVC102, in communication with a channel of a photodiode array. An analog digital converter 320, such as the ADS1241, is positioned in communication with the integrator 310 and interfaced with the main controller unit via an interface 330, such as an SPI interface. As one of ordinary skill in the art will appreciate, the extension of this schematic diagram to any number of photodiode channels, such as the 32 photodiode array depicted in FIG. 3, is straight forward and can be constructed by one of ordinary skill in the art without requiring undue experimentation. It will also be appreciated by one of ordinary skill in the art that due to the possible limitation of the number of I/O pins on a microcontroller of the Main Controller Unit, port expanders 340 can also be used to generate control signals for the integrator 310. For example, each optional port expander can provides as many as 8 extra I/Os and can also be controlled by the microcontroller of the Main controller unit through an $I^2C$ interface 350.

Figure 9:
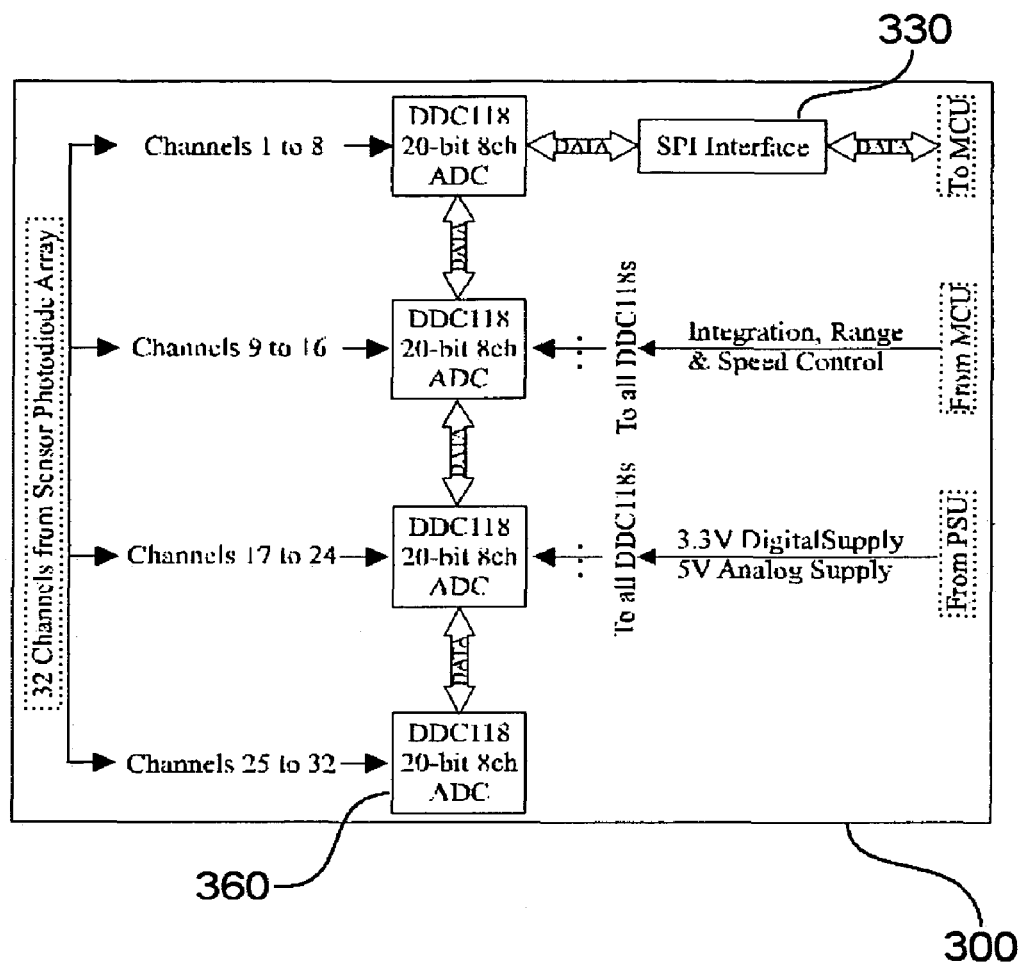
FIG. 9 is an exemplary schematic of a data acquisition unit according to one aspect of the present invention.

In an alternative aspect, and as depicted in the schematic diagram of FIG. 9, the data acquisition unit can comprise one or more current integrating analog to digital converters 360, such as the Texas Instruments DDC118. According to this aspect, the photo detector current from a photo diode in the analyte sensor can be converted to a voltage by the current integrating analog to digital converter. As one of skill in the art will appreciate, the photo detector current will depend, in part, on the responsivity of the particular photo detector used. Thus, as responsivity of the photo detector is increased, the photo detector current will also increase. In one aspect, a photo detector current will typically be of the order of 10 nA. If a photo detector current is not within the measurable range of an analog to digital converter, an appropriately-selected integrating capacitor can be used to adjust the output voltage of the amplifier to a level that is within the measurable range of the analog to digital converter. To this end, the integrating capacitor needed, will depend on the particular level of the photocurrent and the measurable limits of the analog to digital converter. One of skill in the art will readily be able to optimize the integrating capacitor gain without requiring any undue experimentation. In one aspect, an exemplary integrating capacitor will be 3, 12.5, 25, 37.5, 50, 62.5, 75, or 82.5 pF.

The DDC118 is an exemplary and commercially available current-integrating analog to digital converter that can be used with a photo diode as described herein. The DDC118 has integrating capacitors along with a field effect transistor (FET) op-amp which can provide precision voltage corresponding to a particular photo diode current. The signal level can be varied to a desired level by varying the integrating capacitance values and integration times. The DDC118 can periodically sample and convert to a digital value the integrated current from the photo diode and the resulting value can be stored in the memory of the microcontroller of the Main Controller Unit.

Once again, the extension of the schematic diagram of FIG. 9 to any number of photodiode channels, such as the 32 photodiode array depicted in FIG. 3, is straight forward and can be constructed by one of ordinary skill in the art without requiring undue experimentation. It will also be appreciated by one of ordinary skill in the art that due to the possible limitation of the number of I/O pins on a microcontroller of the Main Controller Unit, port expanders can also be used to generate control signals for the current-integrating analog to digital converter. Each optional port expander can provides as many as 8 extra I/Os and can also be controlled by the microcontroller of the Main controller unit through an $I^2C$ interface.

Figure 10:
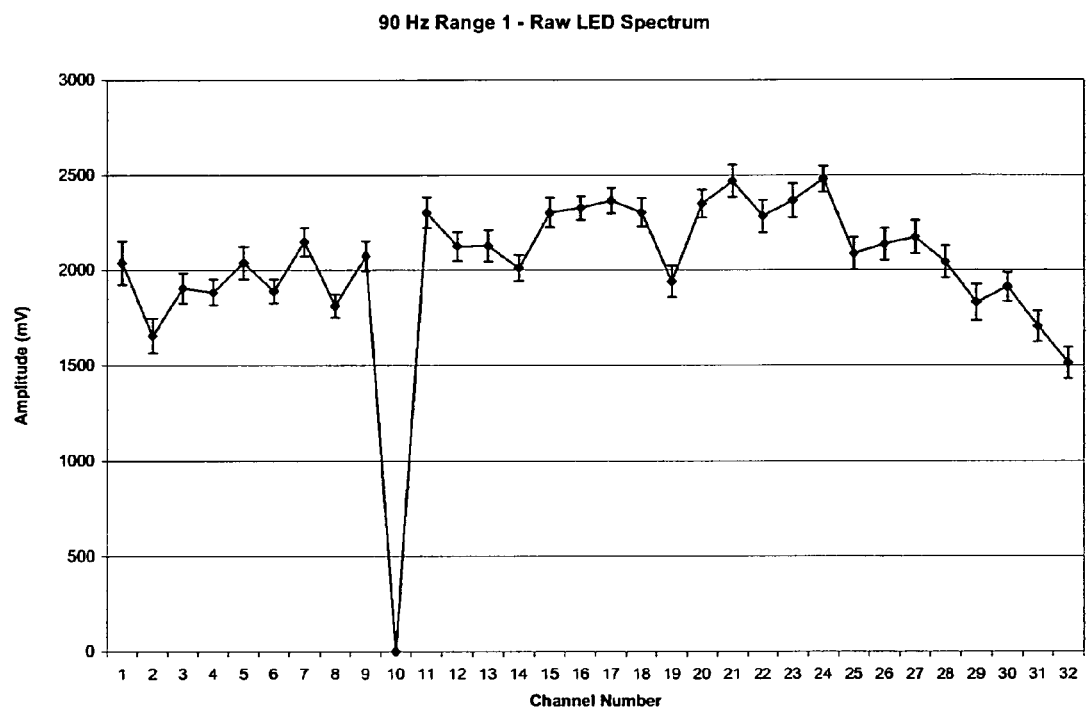
FIG. 10 is a graphical illustration of exemplary digitized data obtained from a data acquisition unit according to one aspect of the present invention. Error bars on the diagram indicate the standard deviation of the noise on the data.
Figure 11:
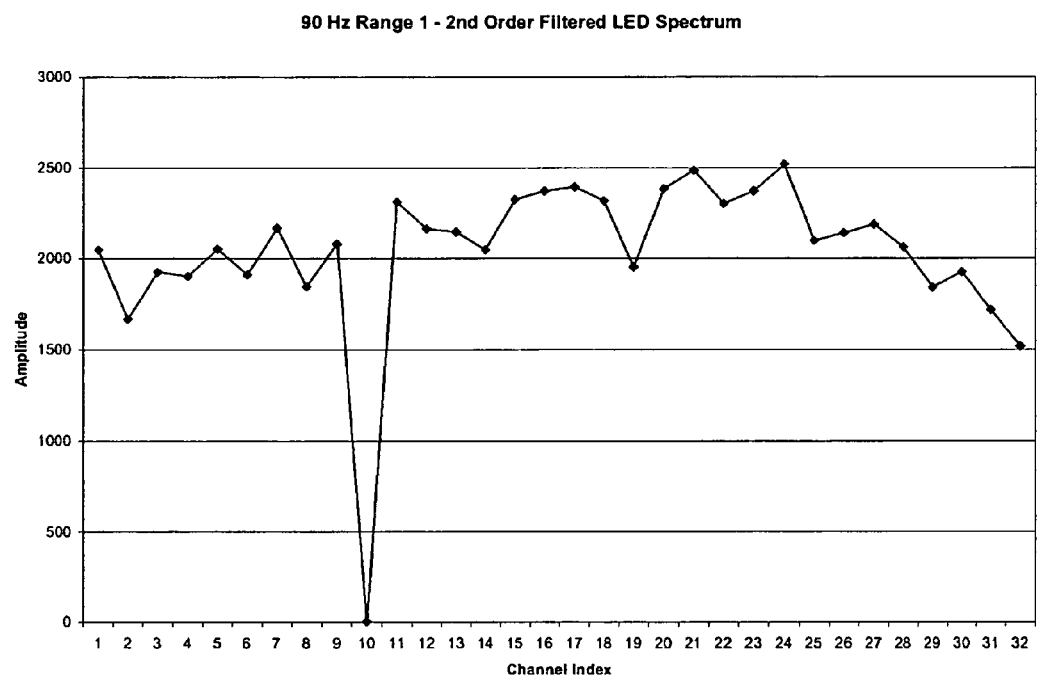
FIG. 11 is a graphical illustration of the exemplary digitized data obtained from a data acquisition unit according to one aspect of the present invention, wherein the signal to noise ratio of the data has been increased by the use of a digital filtering algorithm. No error bars are shown because their width is insignificant on the scale of the drawing.

FIGS. 10 and 11 illustrate exemplary sampled absorption data indicating normalized infrared absorption spectra for a representative glucose containing solution. As depicted, each normalized data point corresponds to the data generated by each channel of a 32 channel photodiode array. The particular data sets were obtained from a current integrating digital analog converter, as described herein, using an exemplary 90 Hz sampling frequency, alternating with 2.5 ms of integration with the infrared LED on and 2.5 ms with the LED off. FIG. 10 indicates raw data obtained from the digital analog converter and FIG. 11 indicates the same data after having been filtered with a digital filtering algorithm designed to increase the signal to noise ratio. These exemplary data point are further indicative of the data which can be time stamped and stored in the main controller unit of the electronic support system and transmitted to the remote telemetry unit for further evaluation.

The electronic support system 200 can further comprise a Power Supply Unit 500 that can provide a regulated power supply to one or more modules and/or components of the electronic support module. It should be understood that the power supply unit can be configured to provide any desired level of regulated voltage, depending on the operational requirements of the individual components present within the analyte sensor and electronic support unit. For example and without limitation, in one aspect the power supply can provide a regulated voltage in the range of from approximately 1.0V to approximately 5.0 volts, including voltages of 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.5, 4.6, 4.7, 4.8, 4.9 and any range derived from these values. In another aspect, the power supply provides a regulated voltage ranging from approximately 3.3 V-5V to one or more modules and/or components of the electronic support module.

Additionally, the power supply unit 500 can also provide power for recharging the batteries. Thus, in one aspect, the PSU 500 can be constructed and arranged to comprise an external remote charger unit 510 and an internal inductive power unit 560. According to this aspect, power can be transmitted electromagnetically by the remote charger unit (RCU) 510 to the inductive power unit (IPU) 560 using transcutaneous inductive coupling.

The IPU 560 can supply regulated power to one or more of the units of the internal module. Again, it should be understood that the internal power unit can be configured to provide any desired level of regulated voltage to the internal module depending on the operational requirement of the internal module. In one aspect, the internal power unit can provide regulated voltage in the range of from approximately 1.0V to approximately 5.0 volts, including voltages of 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.5, 4.6, 4.7, 4.8, 4.9 and any range derived from these values. In another aspect, and without limitation, the internal power unit power supply can provide a regulated voltage ranging from approximately 3.3 V-5V to the internal module.

Figure 12:
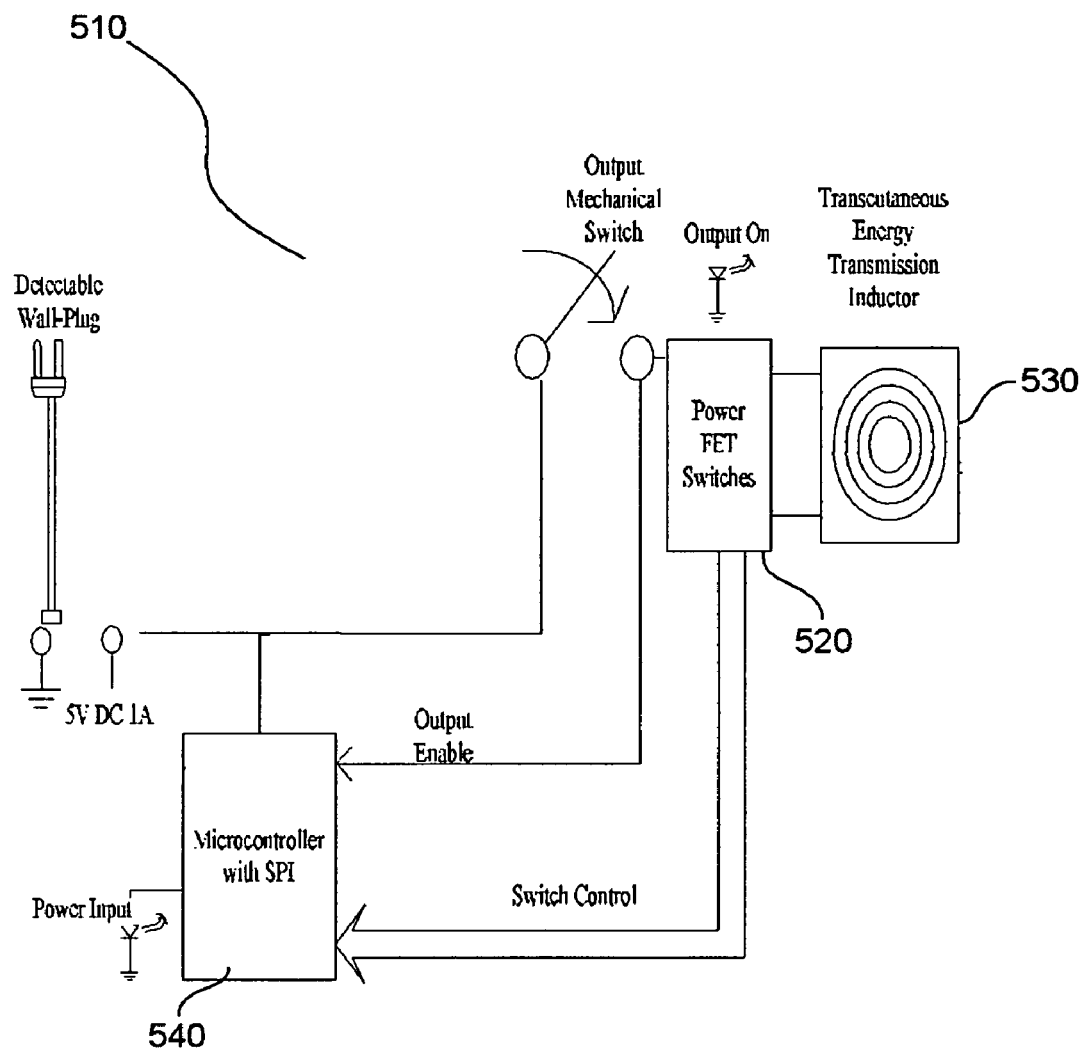
FIG. 12 is an exemplary schematic of a remote charger unit according to one aspect of the present invention.

In one aspect, the IPU power source is comprised of two or more battery packs 580, with each pack containing a pair of rechargeable batteries. According to the exemplified aspect in which the IPU supplies a regulated 3.3 V to the internal module, the pair of rechargeable batteries can be, for example, 1.2 V NiMH batteries having 1600 mAh capacity and being connected in series. In use, at any given time a first battery pack can source electrical power to the internal module while the IPU can recharge the second or plurality of second battery packs. The remote charging unit or RCU can also facilitate the charging of the batteries by using transcutaneous inductive coupling through the use of FET switches 520 and a transcutaneous energy transmission inductor 530. The FET switches can generate square waveforms and can be turned ON and OFF alternatively by a microcontroller 540. A schematic of an exemplary RCU 510 is shown in FIG. 12.

The switching rate of the FET's can in one aspect correspond to the optimal transmission frequency of the inductive power unit. To this end, the optimal FET switch rate can be obtained by one of ordinary skill in the art without any undue experimentation. To this end, in the exemplified aspect set forth herein, the optimal switch rate for the FET's can be approximately 4.7 kHz.

Figure 13:
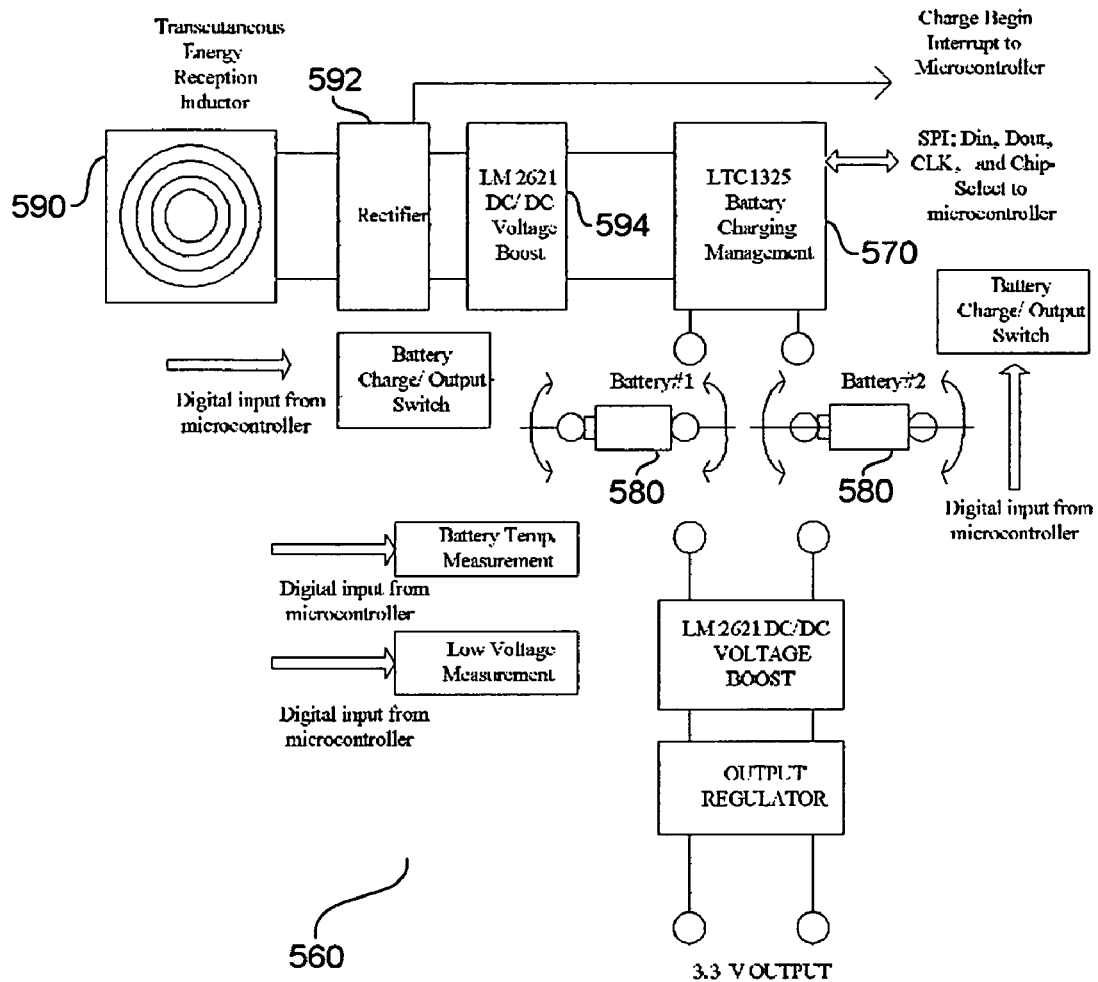
FIG. 13 is an exemplary schematic diagram of an internal power unit according to one aspect of the present invention.

In an exemplary aspect, the IPU 560 can comprise the Linear Technology LTC1325 battery management integrated circuit 570. The LTC1325 is capable of charging a NiMH, Li-ion, and NiCd rechargeable batteries. It is also capable of measuring and/or monitoring battery voltage, battery temperature and/or ambient temperature thereby providing battery status data. The IPU can also comprise its own microcontroller that supervises the LTC1325 through a serial port interface. In use, a fully charged battery pack can have any desired voltage, such as, for example, a voltage of approximately 2.5 V. If needed according to the voltage requirements of the particular system, this voltage can be boosted using an integrated voltage booster circuit and then supplied to a voltage regulator to output a desired voltage, such as, for example, 3.3 V as exemplified above. Accordingly, in one aspect, the IPU is capable of supplying any desired regulated voltage at any desired current load, such as, for example, 700 mAh, in order to power any device within the electronic support unit. A schematic of an exemplary IPU is shown in FIG. 13.

Figure 14:
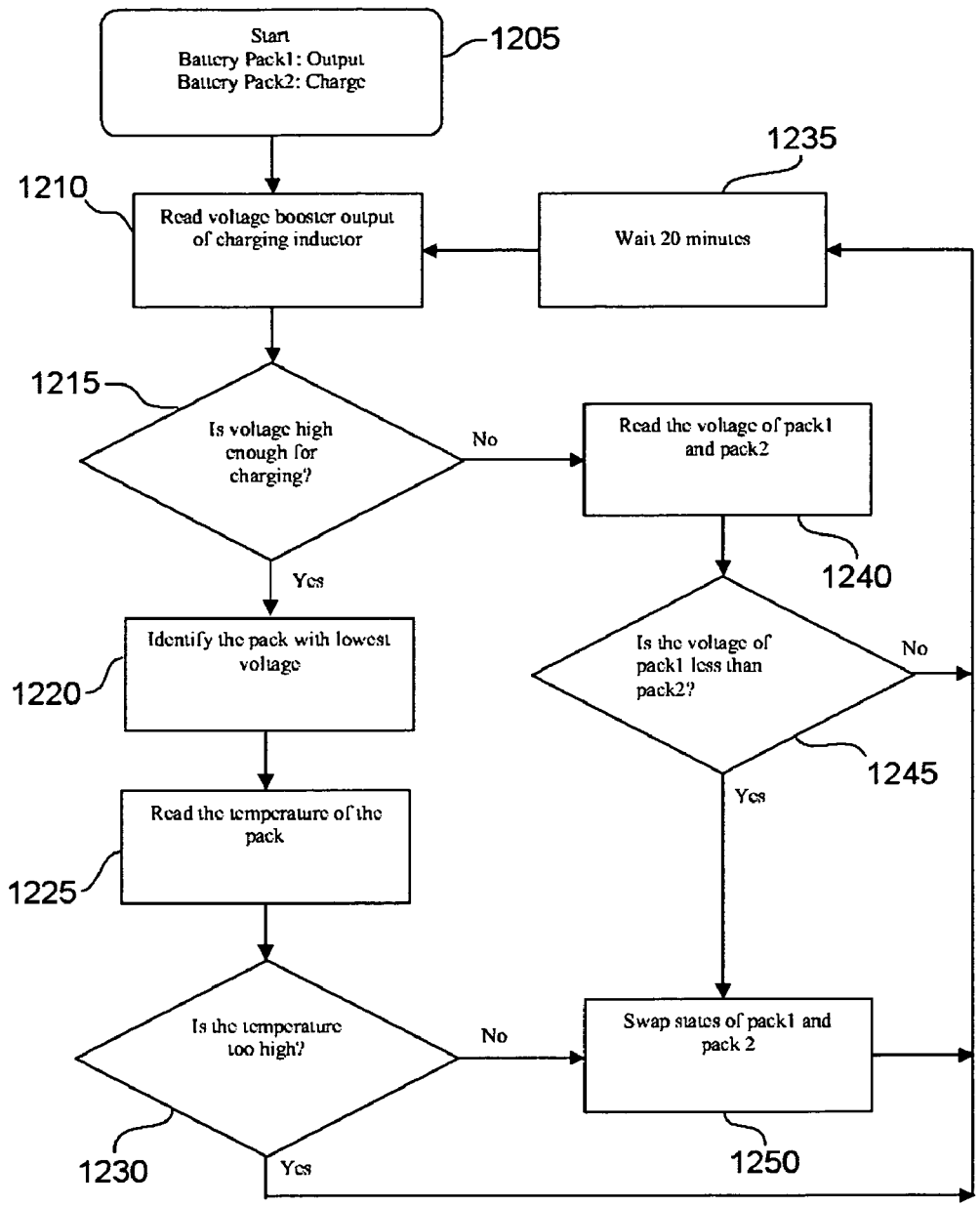
FIG. 14 illustrates a flow chart diagram of a battery charging cycle according to one aspect of the present invention.

In order to receive the transmitted inductive power, the IPU can use an inductor 590 that is similar or identical to the one used for the RCU. In use, the received waveform can be rectified by a rectifier 592 and fed to a voltage booster unit 594, which boosts the voltage to a desired voltage, such as, for example, approximately 5 V. This voltage can then be used to charge a battery pack 580 and to power a battery management integrated circuit 570 such as the LTC1325 battery management integrated circuit described above. The microcontroller of the IPU can also communicate with the battery management circuit and, based upon the varying state of the battery, determine which phase of the charging cycle to enter. Exemplary determinations that can be performed by the IPU microcontroller are depicted in a flow chart as illustrated in FIG. 14. As illustrated, the IPU microcontroller can switch to a charging mode when it detects transmission of power. If no power is being transmitted, the battery pack with lower voltage can be switched to the charging mode and the other battery pack can drive the system. Additionally, while the battery is being charged, the battery temperature can also be monitored in order to prevent overheating during the charge cycle.

More specifically, as exemplified in FIG. 14, at block 1205 a first internal battery pack can provide power to the primary module in an output state while a second battery pack can receive a charge from the RCU in a charge state. For the purpose of the exemplified system the method begins with battery pack one in the output state and battery pack two in the charge state. At block 1210 a voltage booster output of the charging inductor is read. The system then proceeds to perform a check at block 1215 to determine if the voltage read is high enough for charging. If the system determines that voltage is high enough for charging, the system proceeds to block 1220, to identify the battery pack with lowest voltage. Then at block 1225, the system reads the temperature of the pack. At block 1230, the system can perform another check to determine if the temperature is too high. If the system determines that the temperature is too high, the system proceeds to block 1235 and can stand by for a predetermined period of time, such as for example 20 minutes. After the predetermined period of time has lapsed, the system returns to block 1210.

If at block 1215 the voltage booster output is not high enough for charging, the system can then proceed to block 1240. At block 1240, the system can read the voltage of battery pack one and battery pack two. Then, at block 1245, the system performs a check to determine the relative voltages of the battery packs, i.e., if the voltage of battery pack one is less than the voltage of battery pack two. If the voltage of battery pack one is less than the voltage of battery pack two the system proceeds to block 1250 and swaps the states of battery packs one and two. If at block 1245 the voltage of battery pack one is not less than the voltage of battery pack two, the system proceeds to block 1235 and can standby for a predetermined period of time before returning to block 1210.

The electronic support system further comprises a telemetry unit 600 or (TU) that can provide a wired or wireless interface between the internal module and the external module. Examples of wireless telemetry connections can include RF, Infrared, 802.xxx, satellite, cellular, and the like. The external module can in one aspect be integrated into a user's personal computer or PDA. Alternatively, the external module can also be a stand alone device. In one aspect, RF telemetry can enable reliable transmission of sensor data on a full-duplex wireless link from the mobile implanted sensor to an external base station. Data can then be collected and sent as packets using a radio protocol that incorporates error detection in order to ensure data accuracy. These packets can also be transmitted to the receiver in any desired frequency, such as, for example, in five minute intervals.

The telemetry unit also comprises a receiving unit that is capable of receiving the data, acknowledging the receipt of valid data, decoding data, and checking for transmission errors. The receiving unit can be interfaced to a PC based system, which can also be integrated into an internet Web based application that can permit local and or remote data analysis by the patient and/or one or more medical health professionals.

Figure 15:
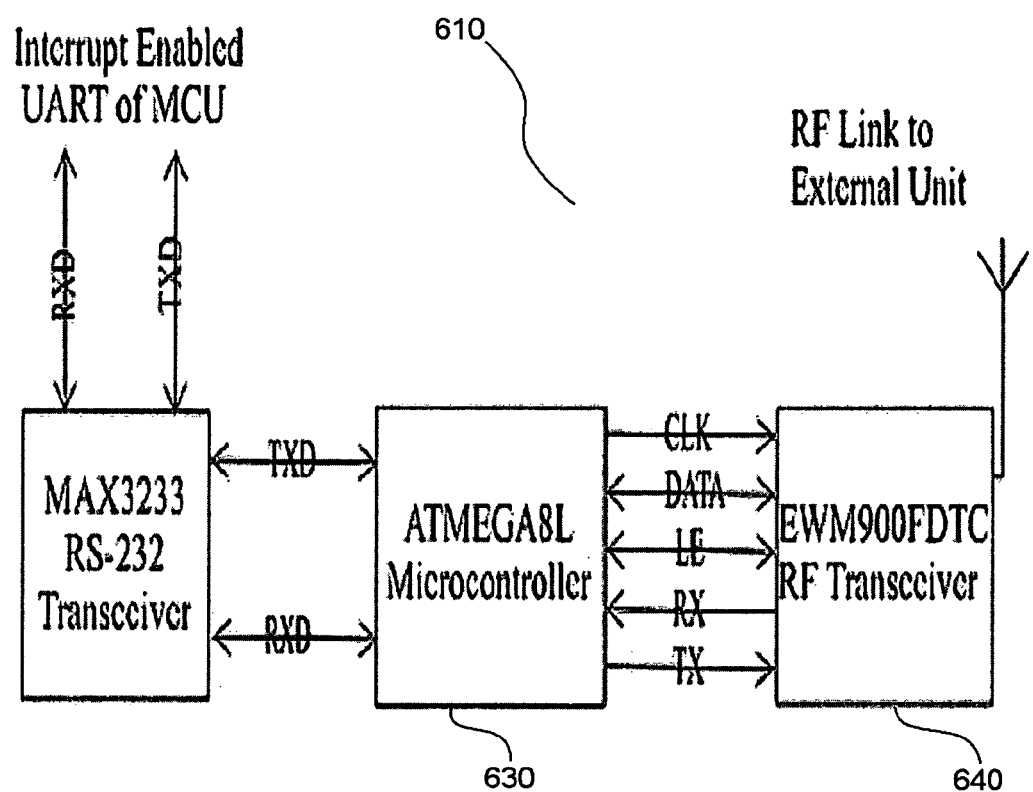
FIG. 15 illustrates an exemplary schematic diagram of an internal telemetry unit according to one aspect of the present invention.
Figure 16:
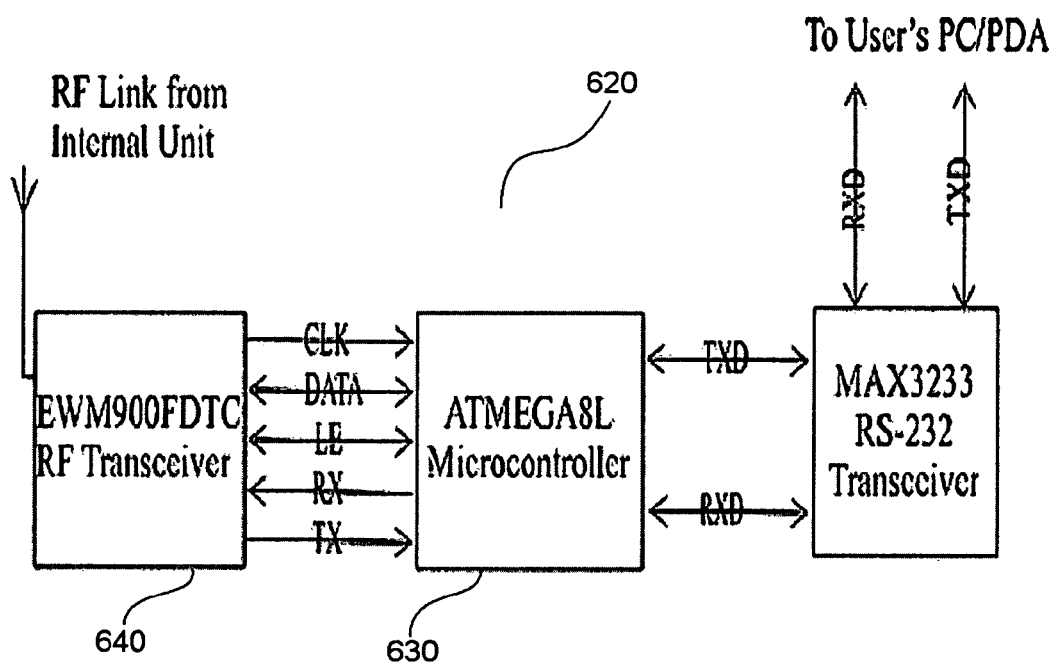
FIG. 16 illustrates an exemplary schematic diagram of an external telemetry unit according to one aspect of the present invention.

The RF telemetry system can also comprise a first internal or primary telemetry unit 610 which forms a part of the primary module. A remote telemetry unit 620 can also be provided and can be integrated into the remote or external module. Schematic diagrams of an exemplary internal 610 and external telemetry unit 620 are illustrated in FIGS. 15 and 16 respectively. The internal telemetry unit can be similar to or the same as the external unit but is powered by the rechargeable battery power supply. The TU can also be interfaced to both the main controller unit and the power supply unit through conventional interrupt driven protocols.

As will be appreciated upon practicing the invention disclosed herein, the external telemetry unit can enable user access to data through a base station. The external telemetry unit can therefore comprise a microcontroller based system and an RS-232 transceiver. To this end, the block diagram shown in FIG. 16 illustrates an exemplary external telemetry unit comprised of an Atmel Atmega8L AVR microcontroller 630 interfaced to a radio transceiver EWM-900-FDTC 640 through a 3-wire serial interface. If desired, an antenna input can act as the transmitting and the receiving conductor. In one aspect, the antenna input has an impedance of approximately 50 ohms. Digital signals can also be sent to the RF transmitter through the 3-wire serial interface and subsequently converted to radio signals using FM/FSK modulation and then transmitted using the antenna.

The internal telemetry unit is capable of sending sensor data to the external telemetry unit and can also be configured to wait for acknowledgments from the external unit. The internal unit can, in one aspect, transmit 24-bit sensor data along with time stamp information, 16-bit CRC and protocol overhead to the external unit. The radio signals transmitted from the internal telemetry unit can then be received by the external unit through an antenna and converted to digital signals compatible with the CMOS levels for the microcontroller using I/Q demodulation. The received data can also be sent through the UART to a PC or PDA and made accessible to the user. Depending on the choice of components used in the telemetry unit, baud rates of at least 9600 can be used for the data transmission described above. In another aspect, the baud rate can be at least 14400, at least 19200, at least 38400, at least 56000, at least 128000, or at least 256000. To this end, any baud rate capable of providing the data transmission described above can be used in accordance with the present invention.

In another aspect, the internal telemetry unit can be configured to communicate with a remote web server via a network connection, such as over the Internet. The network connection can be, for example, a wired or wireless connection. Examples of wireless connections can include RF, Infrared, 802.xxx, satellite, cellular, and the like. Still further, the internal telemetry unit can be configured to communicate by any one or more of the foregoing exemplary wired or wireless connections. For example, a primary module of the instant invention can be configured to connect to any available 802.xxx connection and transmit sampled biological data to a remote server. Additionally, the sampled data can be encrypted or decrypted as needed. When the primary module is not in range of an available 802.xxx connection, the telemetry can be programmed to automatically switch to a subsequently available communication network.

As described, the ESU can be constructed and arranged to operate continuously and unobtrusively for extended durations with minimal or even no user intervention. Owing to the conditions and the environment in which the sensor and ESU operate, as stated above, in one aspect, a battery based power supply capable of remote charging can be used. It will be also be appreciated upon practicing the present invention that data loss, which can occur when, for example, a user is out of communicable range from the base station for an extended period of time, can be prevented by features implemented in firmware. For example, the ESU can be configured to operate at a relatively low power supply voltage, such as 3.3 V, for reduced power consumption. To this end, a power supply according to this aspect can typically provide more than 24 hours of continuous energy in between successive battery recharge cycles at constant maximum discharge current of, for example, approximately 100 mA. Further, a low power operation mode or sleep mode can be supported as described above in order to conserve the battery energy when the analyte data is not being sampled.

Exemplary and non limiting system specifications concerning data memory capacity, power supply voltage, battery capacity, sampling rate, and data transfer rate are listed in Table 2 below for one aspect of the instant invention.

TABLE 2

| Specifications | Units | Target Value |
| --- | --- | --- |
| Memory Capacity | kB | 32 |
| Power Supply | V | 3.3 |
| Battery Capacity | mAh | 3200 |
| Sampling Rate (max) | Hz | 15 |
| Data Transfer Rate | kbps | 13 |
| Serial Interface | Type | SPI, I²C, RS-232 |

Figure 17:
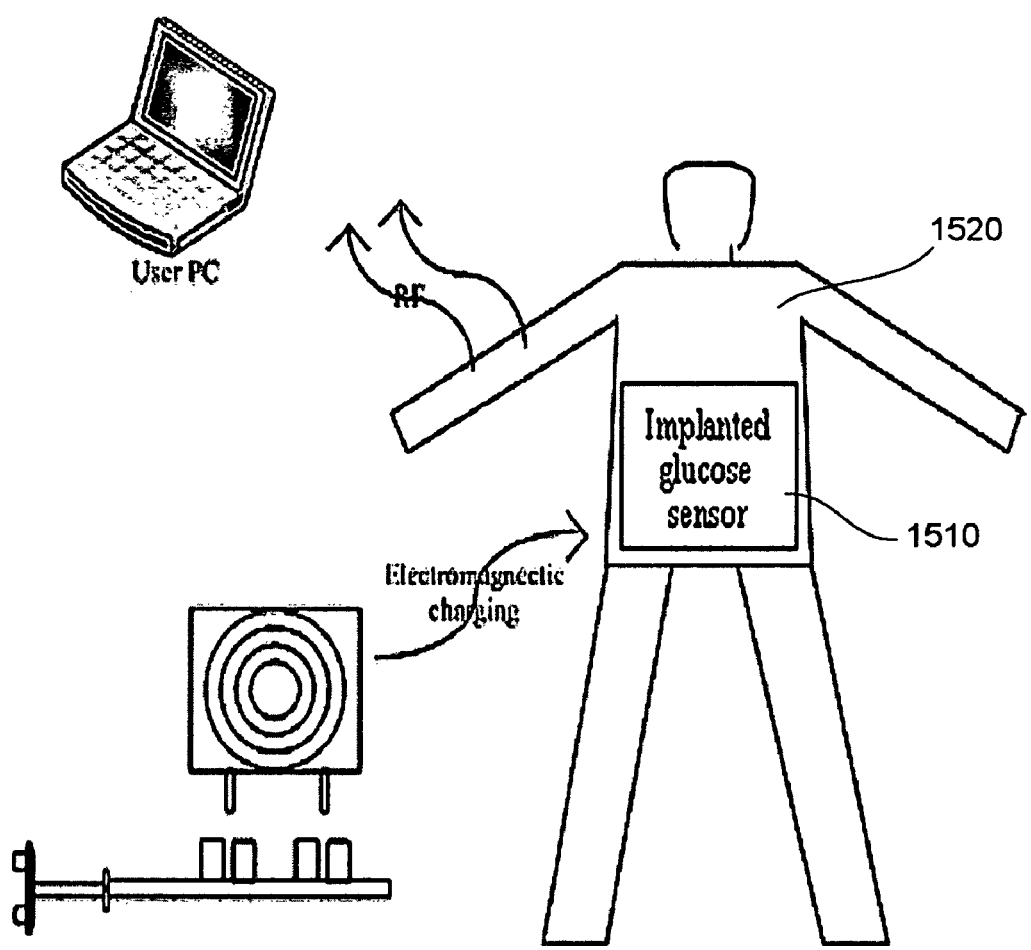
FIG. 17 illustrates an exemplary physical implantation and use of an electronic support unit and analyte sensor according to the present invention.
Figure 18:
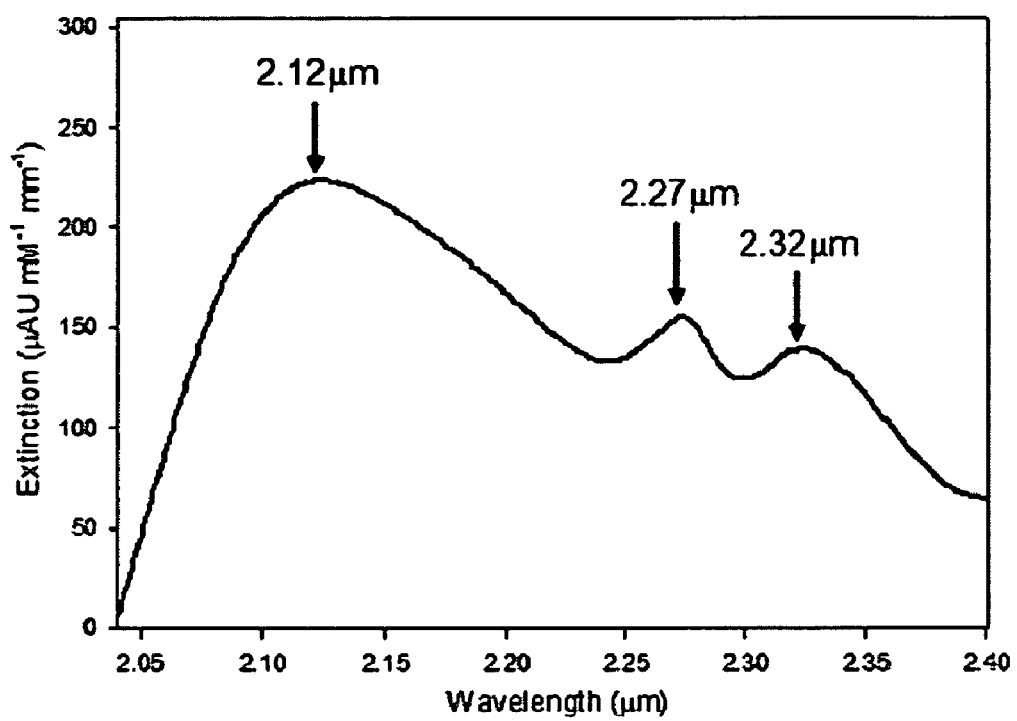
FIG. 18 illustrates the near infrared absorption spectrum for glucose in the spectral range of from approximately 2.05 µm to approximately 2.4 µm.

FIG. 17 illustrates an exemplary physical implementation of an analyte sensor 1510 into a test subject 1520. In use, the sensor can be implanted in the subcutaneous tissues of, for example, the human body. The ESU can enable the sensor to operate for months with minimal user intervention. During operation, the interstitial fluid from subcutaneous space can be sampled through an embedded ultra filtration probe and can then enter into a micro fluidic chamber, which can be physically isolated from the biological environment. If, for example, glucose is the analyte under investigation, then the sample can be carried to an optimized spectrometer cell, where a 16 cm$^{-1}$ resolution near infrared spectrum is collected over a spectral range of from approximately 4600 to approximately 4200 cm$^{-1}$ (2.17-2.38 μm). The uniqueness of the glucose spectrum in this waveband is illustrated in FIG. 18. The concentration of the glucose can then be obtained from direct analysis of the collected absorbance data in the selected waveband. As one of ordinary skill in the art will appreciate, the spectral range illustrated above is optimized for use in connection with glucose. Thus, the desired spectral range will be dependent upon the particular analyte under investigation.

The electronic support unit described and disclosed herein can be used in a variety of applications. As such, in another aspect, the present invention provides a method for performing any one or more of the applications disclosed herein, wherein the method further comprises utilization of an ESU as described herein. For example, the ESU can be used in connection with analyte concentration measurement, analysis, data logging, storage, and/or transmission. In one aspect, the analysis of an analyte concentration in a test subject can be accomplished by using an order derivative of the absorption data collected by the data acquisition unit, including zero order, optionally combined with other forms of data pre-processing. Any statistical technique may be used to derive the primary calibration algorithm, for example, which should not be considered limiting in any way, simple linear regression, multiple linear regression and multivariate data determination. Examples of multivariate data analysis, which should not be considered limiting in any way, are principle component analysis, principle component regression, partial least squares regression, and neural networks. Examples of data pre-processing, which should also not be considered limiting in any way, can include smoothing, deriving a first higher order derivative of absorbance, interpolation of absorbance, multiplicative scatter correction, photometric correction, and data transformation, such as Fourier Transform.

In one aspect, a computing apparatus for computing and analyzing the analyte concentration from the data transmitted to the external telemetry unit can comprise a processor such as a microprocessor, a hybrid/software system, controller, computer, neural network circuit, digital signal processor, digital logic circuits, or an application specific integrated circuit, and memory. The computing apparatus can be electronically coupled to the data received by the external telemetry unit and can contain circuits programmable to perform mathematical functions such as, for example, waveform averaging, amplification, linearization, signal rejection, differentiation, integration, network or fuzzy logic, addition, subtraction, division, multiplication, and the like where desired.

In an alternative aspect, and apart from assisting a user, physician or other medical professional in monitoring analyte levels, such as blood glucose levels of patients in real time, the sensor unit comprising an ESU as described herein can in another aspect be used as a feedback element in an insulin delivery system, where, for example, the entire system can function as an artificial pancreas. Thus, in another aspect, the present invention provides an artificial biological delivery system comprising an ESU as described herein.

Figure 19:
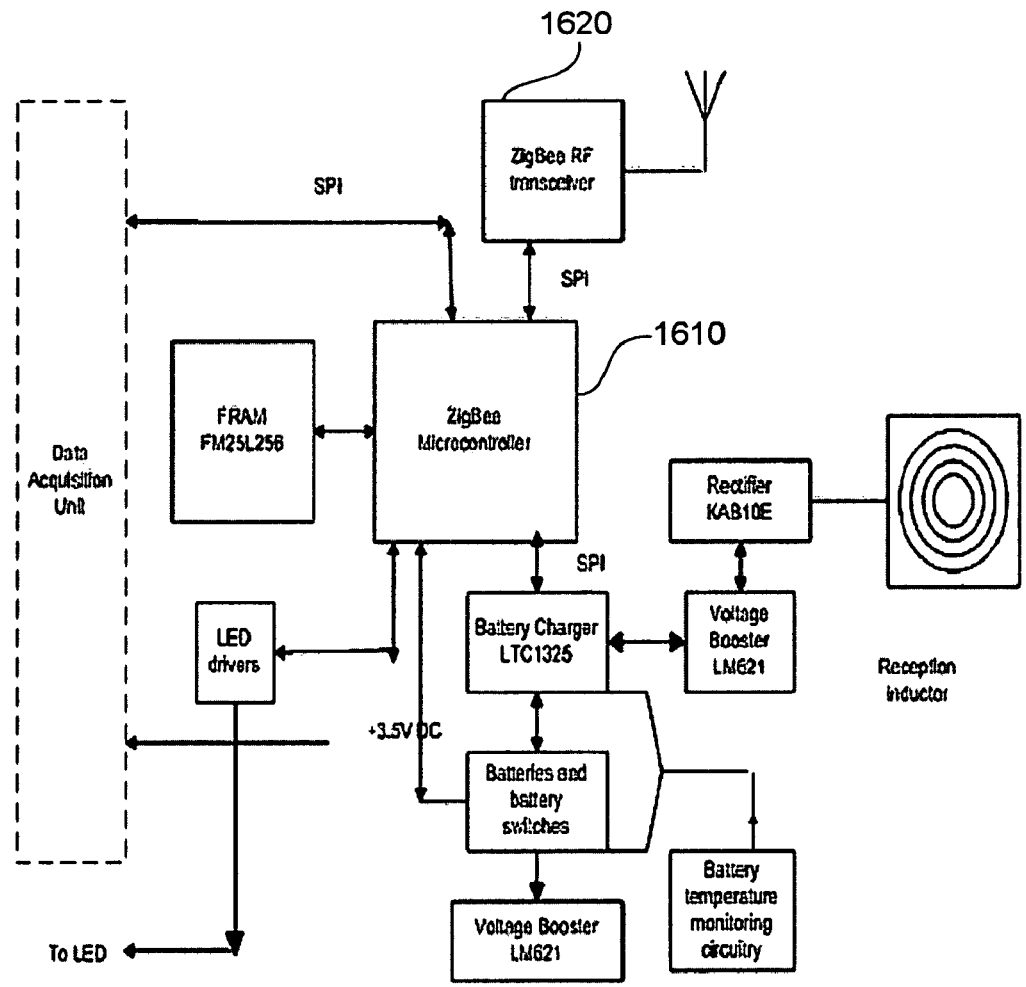
FIG. 19 illustrates an exemplary schematic diagram of an internal module according to an alternative aspect of the present invention.
Figure 20:
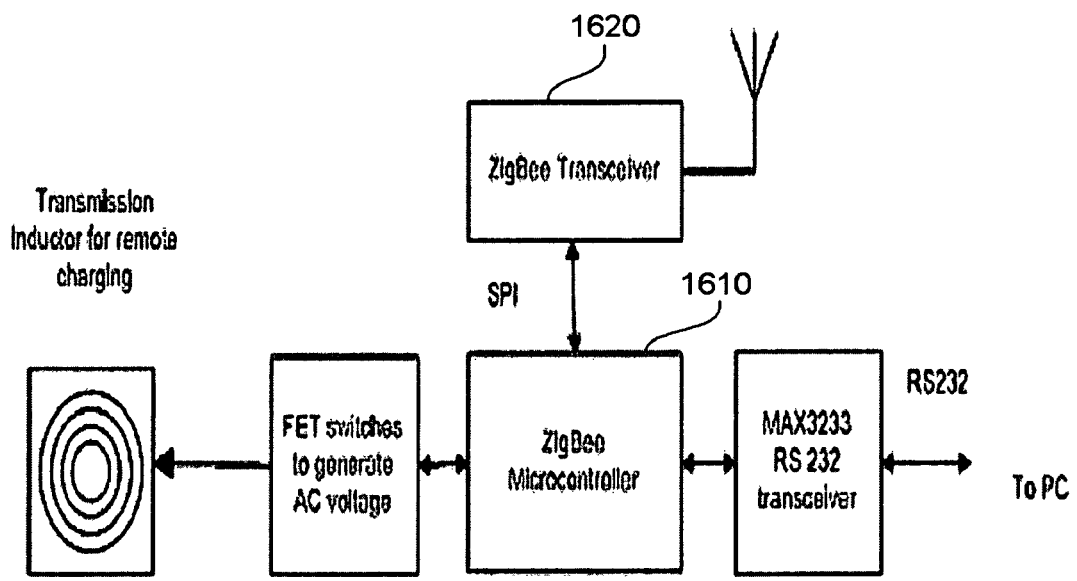
FIG. 20 illustrates an exemplary schematic diagram of an external module according to an alternative aspect of the present invention.

In still another aspect, the electronic support system can be adapted for use with a plurality of other sensor units involving the measurement of biological data. For example, individual sensor units can be adapted to function as nodes of a larger network through the use of the ESU's adaptable telemetry unit. For example, use of a ZigBee 802.15.4 protocol based microcontroller 1610 and transceiver 1620 can be used in the instant invention. IEEE 802.15.4 is a wireless technology protocol standard targeted at home networking and sensor networks and, when used, can permit up to, for example, 255 nodes to exist in one network. It is an ultra low power technology with relatively low system hardware requirements and can provide up to 250 kbps of bandwidth. Thus, the use of 802.15.4 technology in the instant invention can provide an ESU having reduced power consumption and increased security in transmissions. Still further, any desired number of such networks could be set up in, for example, a hospital and the nodes (individual sensor units) could all be controlled remotely from a central location. FIGS. 19 and 20 illustrate alternative aspects of the instant invention comprised of components using the 802.15.4 based ZigBee protocol.

In view of the foregoing, it will be apparent to those skilled in the art that various modifications and variations can be made in the present invention without departing from the scope or spirit thereof. As such, other aspects of the present invention will become apparent to those skilled in the art from consideration of the instant specification and practice of the invention disclosed herein.

What is claimed is:

1. An implantable microspectrometer, comprising:
    an optical sampling cell within a cell housing, said cell housing further defining a fluid inlet port and a fluid outlet port, the fluid inlet port configured to receive an optical sampling fluid from a test subject;
    an electromagnetic radiation source in communication with a first portion of the optical sampling cell housing and configured to irradiate at least a portion of the optical sampling fluid with electromagnetic radiation; and
    an electromagnetic radiation detector in communication with a second portion of the optical sampling cell housing and configured to detect electromagnetic radiation emanating from the optical sampling cell,
    wherein the implantable microspectrometer can optically detect at least one parameter of an analyte contained within the optical sampling fluid in the absence of a reagent, and wherein the implantable microspectrometer occupies a total volume in the range of from about 0.01 cm$^3$ to about 1.0 cm$^3$.

2. The implantable microspectrometer of claim 1, wherein the electromagnetic radiation source comprises a light emitting diode.

3. The implantable microspectrometer of claim 2, wherein the light emitting diode comprises GaInAsSb.

4. The implantable microspectrometer of claim 2, wherein the light emitting diode comprises a cascade of two or more p-i-n junction emitter regions.

5. The implantable microspectrometer of claim 2, wherein the light emitting diode exhibits a maximum voltage draw less than about 4.0 volts and a maximum current draw less than about 30 mA.

6. The implantable microspectrometer of claim 5, wherein the infrared electromagnetic radiation is in the spectral range of from 4000 cm$^{-1}$ to 6500 cm$^{-1}$.

7. The implantable microspectrometer of claim 5, wherein the infrared electromagnetic radiation is in the spectral range of from 300 cm$^{-1}$ to 4000 cm$^{-1}$.

8. The implantable microspectrometer of claim 1, wherein the electromagnetic radiation source is configured to generate infrared electromagnetic radiation.

9. The implantable microspectrometer of claim 1, wherein the electromagnetic radiation source is connected to the first portion of the optical sampling cell housing.

10. The implantable microspectrometer of claim 1, wherein the radiation detector comprises a photodiode array comprising a plurality of photodiode detector elements.

11. The implantable microspectrometer of claim 10, wherein the photodiode array comprises an array of from 16 to 64 photodiode detector elements.

12. The implantable microspectrometer of claim 10, wherein the photodiode array has a specific detectivity of from about $10^8$ cmHz$^{1/2}$ watt to about $10^{12}$ cmHz$^{1/2}$ watt.

13. The implantable microspectrometer of claim 10, wherein the photodiode array comprises a plurality of solid state p-i-n photo diodes.

14. The implantable microspectrometer of claim 13, wherein the plurality of solid state p-i-n photodiodes comprise GaInAsSb, InGaAs, PbS, PbSe, or any combination thereof.

15. The implantable microspectrometer of claim 14, wherein the infrared electromagnetic radiation is in the spectral range of from 4000 cm$^{-1}$ to 6500 cm$^{-1}$.

16. The implantable microspectrometer of claim 14, wherein the infrared electromagnetic radiation is in the spectral range of from 300 cm$^{-1}$ to 4000 cm$^{-1}$.

17. The implantable microspectrometer of claim 1, wherein the electromagnetic radiation detector is configured to detect infrared electromagnetic radiation.

18. The implantable microspectrometer of claim 1, wherein the electromagnetic radiation detector is capable of substantially continuous operation while maintaining a detector temperature less than about 100° F.

19. The implantable microspectrometer of claim 18, wherein the bandpass filter comprises a passband width of from approximately 12 cm$^{-1}$ to approximately 20 cm$^{-1}$.

20. The implantable microspectrometer of claim 1, wherein the electromagnetic radiation detector comprises a bandpass filter.

21. The implantable microspectrometer of claim 1, wherein the electromagnetic radiation detector is connected to the second portion of the optical sampling cell housing.

22. The implantable microspectrometer of claim 1, wherein the optical sampling cell housing is comprised of an electromagnetic radiation transparent material.

23. The implantable microspectrometer of claim 22, wherein the electromagnetic radiation transparent material comprises a fluoropolymer.

24. The implantable microspectrometer of claim 1, wherein the optical sampling cell is substantially cylindrical in shape.

25. The implantable microspectrometer of claim 24, wherein the optical sampling cell has a diameter in the range of from approximately 150 µm to approximately 250 µm, an optical path length in the range of from approximately 0.5 mm to approximately 1.5 mm, and an interior volume in the range of from approximately 25 nL to approximately 35 nL.

26. The implantable microspectrometer of claim 1, wherein the optical sampling cell is substantially rectangular in shape.

27. The implantable microspectrometer of claim 1, further comprising a vacuum source in communication with the fluid outlet port of the sampling cell and configured to generate a flow of fluid sample from the test subject, through the fluid inlet port, through the optical sampling cell, and through the fluid outlet port.

28. The implantable microspectrometer of claim 27, wherein the vacuum source is configured to generate a flow of fluid sample having a flow rate in the range of from about 30 nL/min to about 150 nL/min.

29. The implantable microspectrometer of claim 1, further comprising a fluid sampling assembly in communication with the sample fluid inlet port and configured to obtain a fluid sample containing an analyte from a test subject.

30. The implantable microspectrometer of claim 29, wherein the fluid sampling assembly comprises an implantable ultrafiltration probe.

31. The implantable microspectrometer of claim 29, wherein the fluid sampling assembly comprises an implantable microdialysis probe.

32. The implantable microspectrometer of claim 29, wherein the fluid sampling assembly is configured to obtain an interstitial fluid sample from the test subject.

33. The implantable microspectrometer of claim 1, wherein the optical detection of at least one parameter of an analyte contained within the optical sampling fluid comprises the detection of electromagnetic radiation absorption, reflection, scattering, or a combination thereof.

34. The implantable microspectrometer of claim 1, wherein at least one component of the microspectrometer is in electronic communication with an electronic support unit.

35. An implantable microspectrometer for the reagentless optical detection of an analyte in fluid sample, comprising
an optical sampling cell within a cell housing, said cell housing further defining a fluid inlet port and a fluid outlet port, the fluid inlet port configured to receive an optical sampling fluid from a test subject;
a means for generating electromagnetic radiation, whereby the means for generating radiation is in communication with a first portion of the optical sampling cell housing and configured to irradiate at least a portion of the optical sampling fluid with electromagnetic radiation;
a means for detecting electromagnetic radiation, whereby the means for detecting electromagnetic radiation is in communication with a second portion of the optical sampling cell housing and configured to detect electromagnetic radiation emanating from the optical sampling cell,
wherein the implantable microspectrometer can optically detect at least one parameter of an analyte contained within the optical sampling fluid in the absence of a reagent, and wherein the implantable microspectrometer occupies a total volume in the range of from about 0.01 cm$^3$ to about 1.0 cm$^3$.

36. A method for the reagentless optical detection of an analyte in a fluid sample, comprising the steps of:
providing a microspectrometer, comprising: (i) an optical sampling cell within a cell housing, said cell housing further defining a fluid inlet port and a fluid outlet port, the fluid inlet port; (ii) an electromagnetic radiation source in communication with a first portion of the optical sampling cell housing; and (iii) an electromagnetic radiation detector in communication with a second portion of the optical sampling cell housing;
obtaining a fluid sample containing an analyte from a test subject;
conveying the obtained fluid sample through the inlet port in to the optical sampling cell;
generating electromagnetic radiation from the electromagnetic radiation source and irradiating at least a portion of the fluid sample within the optical sampling cell;
optically detecting electromagnetic radiation emanating from the optical sampling cell with the electromagnetic radiation detector; and
returning at least a portion of the obtained fluid sample contained within the optical sampling cell to the test subject,
wherein the microspectrometer occupies a total volume in the range of from about 0.01 cm$^3$ to about 1.0 cm$^3$.

37. The method of claim 36, wherein the fluid sample is a biological fluid.

38. The method of claim 36, wherein the analyte comprises glucose, urea, creatinine, phosphate, sulfate, or a mixture thereof.

39. The method of claim 36, wherein the analyte comprises glucose.

40. The method of claim 36, wherein the fluid sample comprises blood.

41. The method of claim 36, wherein the fluid sample comprises interstitial fluid.

42. The method of claim 36, further comprising implanting the optical sampling cell subcutaneously in the test subject.

43. The method of claim 36 or 42, wherein the fluid sample is obtained from the subcutaneous tissue bed surrounding the peritoneal cavity of a mammalian test subject.

44. The method of claim 36, wherein the electromagnetic radiation detector comprises a photodiode array connected to the optical sampling cell.

45. The method of claim 36, further comprising applying a negative pressure gradient to the optical sampling cell to convey the obtained sample fluid to the optical sampling cell.

46. The method of claim 36 or 45, wherein the portion of the fluid sample conveyed to the optical sampling cell is irradiated with infrared electromagnetic radiation.

47. The method of claim 46, wherein the infrared electromagnetic radiation is in the spectral range of from 4000 cm$^{-1}$ to 6500 cm$^{-1}$.

48. The method of claim 46, wherein the infrared electromagnetic radiation is in the spectral range of from 300 cm$^{-1}$ to 4000 cm$^{-1}$.

* * * * *

UNITED STATES PATENT AND TRADEMARK OFFICE
CERTIFICATE OF CORRECTION

| | | |
|---|---|---|
| PATENT NO. | : 8,204,565 B2 | Page 1 of 1 |
| APPLICATION NO. | : 11/397927 | |
| DATED | : June 19, 2012 | |
| INVENTOR(S) | : Arnold et al. | |

It is certified that error appears in the above-identified patent and that said Letters Patent is hereby corrected as shown below:

In the Specifications:

Column 1, lines 14 to 18, the text "The invention described in the foregoing specification has been developed in part with funds received from the National Institutes of Health under grant number DK-64569. The United States Government may have certain rights under this invention." should read --This invention was made with government support under grant number DK-64569 awarded by the National Institutes of Health. The Government has certain rights in the invention.--.

Signed and Sealed this
Fourth Day of September, 2012

David J. Kappos
*Director of the United States Patent and Trademark Office*